US008065011B2

(12) United States Patent
Echauz et al.

(10) Patent No.: US 8,065,011 B2
(45) Date of Patent: Nov. 22, 2011

(54) ADAPTIVE METHOD AND APPARATUS FOR FORECASTING AND CONTROLLING NEUROLOGICAL DISTURBANCES UNDER A MULTI-LEVEL CONTROL

(75) Inventors: Javier Ramón Echauz, Atlanta, GA (US); Brian Litt, Merion Station, PA (US); Rosana Esteller, Marietta, GA (US); George John Vachtsevanos, Marietta, GA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 607 days.

(21) Appl. No.: 11/469,029

(22) Filed: Aug. 31, 2006

(65) Prior Publication Data

US 2007/0142873 A1    Jun. 21, 2007

Related U.S. Application Data

(60) Continuation of application No. 10/358,039, filed on Feb. 4, 2003, now Pat. No. 7,146,218, which is a division of application No. 09/735,364, filed on Dec. 12, 2000, now Pat. No. 6,594,524.

(51) Int. Cl.
*A61N 1/00* (2006.01)
(52) U.S. Cl. ............................. 607/45; 607/6; 607/139
(58) Field of Classification Search ............... 607/6, 45, 607/139
See application file for complete search history.

(56) References Cited

U.S. PATENT DOCUMENTS 3,837,331 A    9/1974   Ross
(Continued)

FOREIGN PATENT DOCUMENTS

GB    2336211 A    10/1999
(Continued)

OTHER PUBLICATIONS

Iasemidis et al., "Spatiotemporal Evolution of Dynamical Measures Precedes Onset of Mesial Temporal Lobe Seizures," Epilepsia, Vo. 35, No. Suppl. 8, pp. 133, 1994.
(Continued)

*Primary Examiner* — Niketa Patel
*Assistant Examiner* — Nicole F Lavert
(74) *Attorney, Agent, or Firm* — Womble Carlyle Sandridge & Rice, LLP

(57) ABSTRACT

An adaptive method and apparatus for forecasting and controlling neurological abnormalities in humans such as seizures or other brain disturbances. The system is based on a multi-level control strategy. Using as inputs one or more types of physiological measures such as brain electrical, chemical or magnetic activity, heart rate, pupil dilation, eye movement, temperature, chemical concentration of certain substances, a feature set is selected off-line from a pre-programed feature library contained in a high level controller within a supervisory control architecture. This high level controller stores the feature library within a notebook or external PC. The supervisory control also contains a knowledge base that is continuously updated at discrete steps with the feedback information coming from an implantable device where the selected feature set (feature vector) is implemented. This high level controller also establishes the initial system settings (off-line) and subsequent settings (on-line) or tunings through an outer control loop by an intelligent procedure that incorporates knowledge as it arises. The subsequent adaptive settings for the system are determined in conjunction with a low-level controller that resides within the implantable device. The device has the capabilities of forecasting brain disturbances, controlling the disturbances, or both. Forecasting is achieved by indicating the probability of an oncoming seizure within one or more time frames, which is accomplished through an inner-loop control law and a feedback necessary to prevent or control the neurological event by either electrical, chemical, cognitive, sensory, and/or magnetic stimulation.

22 Claims, 25 Drawing Sheets

U.S. PATENT DOCUMENTS

| | | | |
|---|---|---|---|
| 3,850,161 A | | 11/1974 | Liss |
| 3,863,625 A | | 2/1975 | Viglione et al. |
| 3,967,616 A | | 7/1976 | Ross |
| 3,993,046 A | | 11/1976 | Fernandez et al. |
| 4,566,464 A | | 1/1986 | Piccone et al. |
| 4,702,254 A | | 10/1987 | Zabara |
| 4,735,204 A | | 4/1988 | Sussman et al. |
| 4,867,164 A | | 9/1989 | Zabara |
| 4,873,981 A | * | 10/1989 | Abrams et al. ............ 607/45 |
| 4,878,498 A | * | 11/1989 | Abrams et al. ............ 607/45 |
| 5,025,807 A | | 6/1991 | Zabara |
| 5,304,206 A | | 4/1994 | Baker, Jr. et al. |
| 5,311,876 A | | 5/1994 | Olsen et al. |
| 5,713,923 A | | 2/1998 | Ward et al. |
| 5,743,860 A | | 4/1998 | Hively et al. |
| 5,857,978 A | | 1/1999 | Hively et al. |
| 5,928,272 A | * | 7/1999 | Adkins et al. ............ 607/45 |
| 5,978,702 A | | 11/1999 | Ward et al. |
| 5,995,868 A | * | 11/1999 | Dorfmeister et al. ...... 600/544 |
| 6,016,449 A | * | 1/2000 | Fischell et al. ............ 607/45 |
| 6,018,682 A | * | 1/2000 | Rise ............................ 607/45 |
| 6,061,593 A | | 5/2000 | Fischell et al. |
| 6,161,045 A | * | 12/2000 | Fischell et al. ............ 607/45 |
| 6,366,813 B1 | * | 4/2002 | DiLorenzo ................. 607/45 |

FOREIGN PATENT DOCUMENTS

| | | |
|---|---|---|
| WO | WO 00/10455 A1 | 3/2000 |

OTHER PUBLICATIONS

Iasemidis et al., "Chaos Theory and Epilepsy", The Neuroscientist, Mar. 1996, vol. 2, No. 2, pp. 118-126.

Grassberger et al., "Characterization of Strange Attractors," Physical Rev. Letters, vol. 50, No. 5, pp. 346-349.

Elger et al., "Seizure Prediction by Nonlinear Time Series Analysis of Brain Electrical Activity," European Journal of Neuroscience, 1998, vol. 10, pp. 786-789.

* cited by examiner

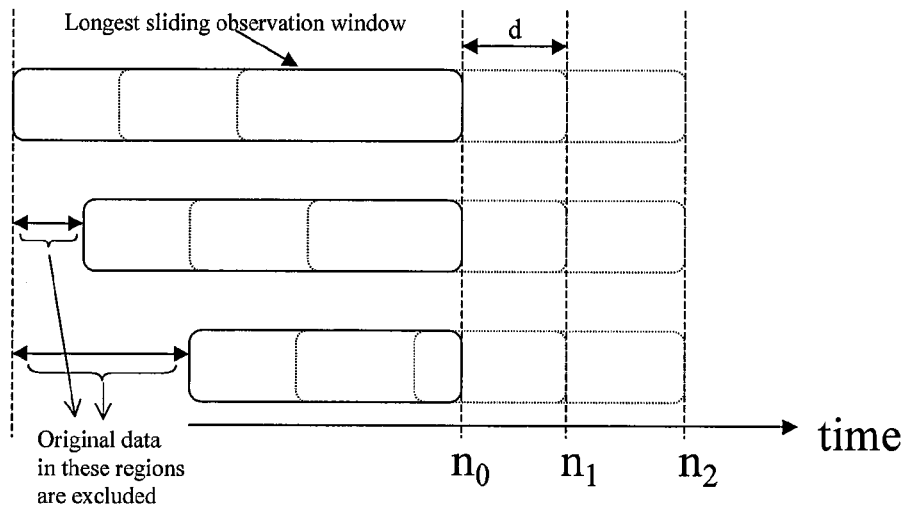
FIG. 28
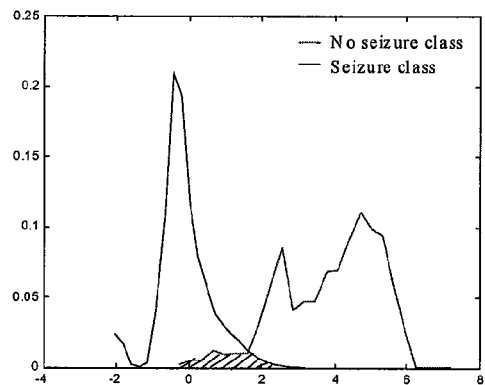 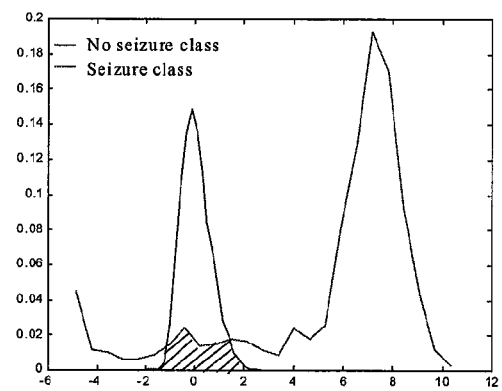
FIG. 29A FIG. 29B

ADAPTIVE METHOD AND APPARATUS FOR FORECASTING AND CONTROLLING NEUROLOGICAL DISTURBANCES UNDER A MULTI-LEVEL CONTROL

CROSS REFERENCE TO RELATED APPLICATIONS

This application is a continuation of U.S. patent application Ser. No. 10/358,039, filed Feb. 4, 2003, now U.S. Pat. No. 7,146,218, issued on Dec. 5, 2006, which is a divisional of U.S. patent application Ser. No. 09/735,364, filed Dec. 12, 2000, now U.S. Pat. No. 6,594,524. The present application is also related to international application WO 00/10455, published under the Patent Cooperation Treaty (PCT) on Mar. 2, 2000, now U.S. Pat. No. 6,658,287 issued on Dec. 2, 2003.

BACKGROUND OF THE INVENTION

The present invention is in the field of prediction and control of neurological disturbances, particularly in the area of electrographic and clinical seizure onset prediction based on implantable devices with the major goal of alerting and/or avoiding seizures.

Approximately 1% of the world's population has epilepsy, one third of whom have seizures not controlled by medications. Some patients, whose seizures reliably begin in one discrete region, usually in the mesial (middle) temporal lobe, may be cured by epilepsy surgery. This requires removing large volumes of brain tissue, because of the lack of a reliable method to pinpoint the location of seizure onset and the pathways through which seizures spread. The 25% of refractory patients in whom surgery is not an option must resort to inadequate treatment with high doses of intoxicating medications and experimental therapies, because of poorly localized seizure onsets, multiple brain regions independently giving rise to seizures, or because their seizures originate from vital areas of the brain that cannot be removed. For these and all other epileptic patients, the utilization of a predicting device would be of invaluable help. It could prevent accidents and allow these patients to do some activities that otherwise would be risky.

Individuals with epilepsy suffer considerable disability from seizures and resulting injuries, impairment of productivity, job loss, social isolation associated with having seizures, disabling side effects from medications and other therapies. One of the most disabling aspects of epilepsy is that seizures appear to be unpredictable. However, in this invention a seizure prediction system is disclosed. Seizure prediction is a highly complex problem that involves detecting invisible and unknown patterns, as opposed to detecting visible and known patterns involved in seizure detection. To tackle such an ambitious goal, some research groups have begun developing advanced signal processing and artificial intelligence techniques. The first natural question to ask is in what ways the preictal (i.e., the period preceding the time that a seizure takes place) intracranial EEGs (IEEGs) are different from all other IEEGs segments not immediately leading to seizures. When visual pattern recognition is insufficient, quantitative EEG analysis may help extract relevant characteristic measures called features, which can then be used to make statistical inferences or to serve as inputs in automated pattern recognition systems.

Typically, the study of an event involves the goals of diagnosing (detecting) or prognosticating (predicting) such event for corrective or preventive purposes, respectively. Particularly, in the case of brain disturbances such as epileptic seizures, these two major goals have driven the efforts in the field. On one hand, there are several groups developing seizure detection methods to implement corrective techniques to stop seizures, and on the other, there are some groups investigating seizure prediction methods to provide preventive ways to avoid seizures. Among the groups claiming seizure prediction, three categories of prediction can be distinguished, clinical onset (CO) prediction, electrographic onset (EO) prediction studies, and EO prediction systems. All these categories in conjunction with seizure detection compose most of the active research in this field.

Related art approaches have focused on nonlinear methods such as studying the behavior of the principal Lyapunov exponent (PLE) in seizure EEGs, computing a correlation dimension or nonlinear chaotic analysis or determining one major feature extracted from the ictal characteristics of an electroencephalogram (EEG) or electrocorticogram (ECoG).

Important Terminology Definitions

Ictal period: time when the seizure takes place and develops.

Preictal period: time preceding the ictal period.

Interictal period or baseline: period at least 1 hour away from a seizure. Note that the term baseline is generally used to denote "normal" periods of EEG activity, however, in this invention it is used interchangeably with interictal period.

Clinical onset (CO): the time when a clinical seizure is first noticeable to an observer who is watching the patient.

Unequivocal Clinical onset (UCO): the time when a clinical seizure is unequivocally noticeable to an observer who is watching the patient.

Unequivocal Electrographic Onset (UEO): also called in this work electrographic onset (EO), indicates the unequivocal beginning of a seizure as marked by the current "gold standard" of expert visual analysis of the IEEG.

Earliest Electrographic Change (EEC): the earliest change in the intracranial EEG (IEEG) preceding the UEO and possibly related to the seizure initiation mechanisms.

Focus Channel: the intracranial EEG channel where the UEO is first observed electrographically.

Focal Adjacent Channel: the intracranial EEG channels adjacent to the focus channel.

Focus Region: area of the brain from which the seizures first originate.

Feature: qualitative or quantitative measure that distills preprocessed data into relevant information for tasks such as prediction and detection.

Feature library: collection of algorithms used to determine the features.

Feature vector: set of selected features used for prediction or detection that forms the feature vector.

Aura: symptom of a brain disturbance usually preceding the seizure onset that may consist of hallucinations, visual illusions, distorted understanding, and sudden, intense emotion, such as anxiety or fear.

FIGS. 11A-11B illustrate some of the defined terms on segments of a raw IEEG signal. Comparison between the preictal segment indicated on FIG. 11A (between the EEC and the UEO times) and the interictal period in FIG. 11B demonstrates the difficulty of discerning between them. The vertical scale in both figures is in microvolts ($\mu V$).

SUMMARY OF THE INVENTION

This invention is an automatic system that predicts or provides early detection of seizure onsets or other neurological events or disturbances with the objective of alerting, aborting or preventing seizures or other neurological ailments by appropriate feedback control loops within multiple layers. One of the main differences from other inventions is that the major functions of the brain implantable device is forecasting and preventing seizures or other brain disturbances rather than only detecting them. Unlike other inventions, the goal is to predict the electrographic onset of the disturbance or seizure rather than the clinical onset. Seizure UEO detection is also accomplished as a direct consequence of the prediction and as a means to assess device performance. Furthermore, the innovative presence of a supervisory control provides the apparatus with a knowledge updating capability supported by the external PC or notebook, and a self-evaluation proficiency used as part of the feedback control to tune the device parameters at all stages, also not present in the other art.

The approach disclosed in the present invention, instead of focusing on nonlinear methods, or on one particular feature, targets multiple features from different domains and combines them through intelligent tools such as neural networks and fuzzy logic. Multiple and synergistic features are selected to exploit their complementarity. Furthermore, rather than using a unique crisp output that considers one particular time frame, as the previous methods introduced, the system provides one or more probabilistic outputs of the likelihood of having a seizure within one or more time frames. Based on this, when a threshold probability is reached, an approaching seizure can be declared. The use of these multiple time frames and probabilistic outputs are other distinct aspects from previous research in the field.

The system possesses multiple levels of closed-loop control. Low-level controls are built up within the implantable device, and consist of brain stimulation actuators with their respective feedback laws. The low-level control operates in a continuous fashion as opposed to previous techniques that provide only one closed-loop control that runs only during short times when the seizure onset is detected. The high-level control is performed by a supervisory controller which is achieved through an external PC or notebook. By using sophisticated techniques, the prediction system envisioned allows the patients or observers to take appropriate precautions before the seizure onset to avoid injuries. Furthermore, the special design of the apparatus furnishes powerful techniques to prevent or avoid seizures and to obtain more insight into these phenomena, thereby revealing important clinical information. The innovative use of a supervisory control is the option that confers the apparatus its unique perspective as a warning/control/adaptive long-term device. The warning is achieved by forecasting the disturbance; the control is accomplished by an appropriate feedback law and a knowledge base update law; and the adaptive capability of the device is attained also by the knowledge base update law driven by the supervisory control. This knowledge base resides in an external personal computer (PC) or notebook that is the heart of the supervisory control, where the apparatus computes optimization routines, and self-evaluation metrics to establish its performance over time, to determine required adjustments in the system set points and produce an updating law that is fed back into the system from this higher level of control.

The control law provided in the device allows a feedback mechanism to be implemented based on electrical, chemical, cognitive, intellectual, sensory and/or magnetic brain stimulation. The main input signal to the feedback controller is the probability of having a seizure for one or more time frames. The supervisory control is based on an external control loop, operating at a higher control level, that compiles new information generated at the implantable device into the knowledge base at discrete steps and provides set point calculations based on optimizations performed either automatically, or semi-automatically by the doctor or authorized individual.

The above and other novel features, objects, and advantages of the invention will be understood by any person skilled in the art when reference is made to the following description of the preferred embodiments, taken in conjunction with the accompanying drawings.

BRIEF DESCRIPTION OF THE DRAWINGS

FIG. 28 illustrates how features are aligned to conform the feature vector and how the span used is the same for features generated with different window lengths.

FIGS. 29A-29B illustrate graphs that are proportional to the probability density functions (pdfs) of the feature fractal dimension for each of the classes defined in two different patients. Note the overlap region between the classes is marked with the cross-hatched lines.

DETAILED DESCRIPTION OF THE INVENTION

Figure 1:
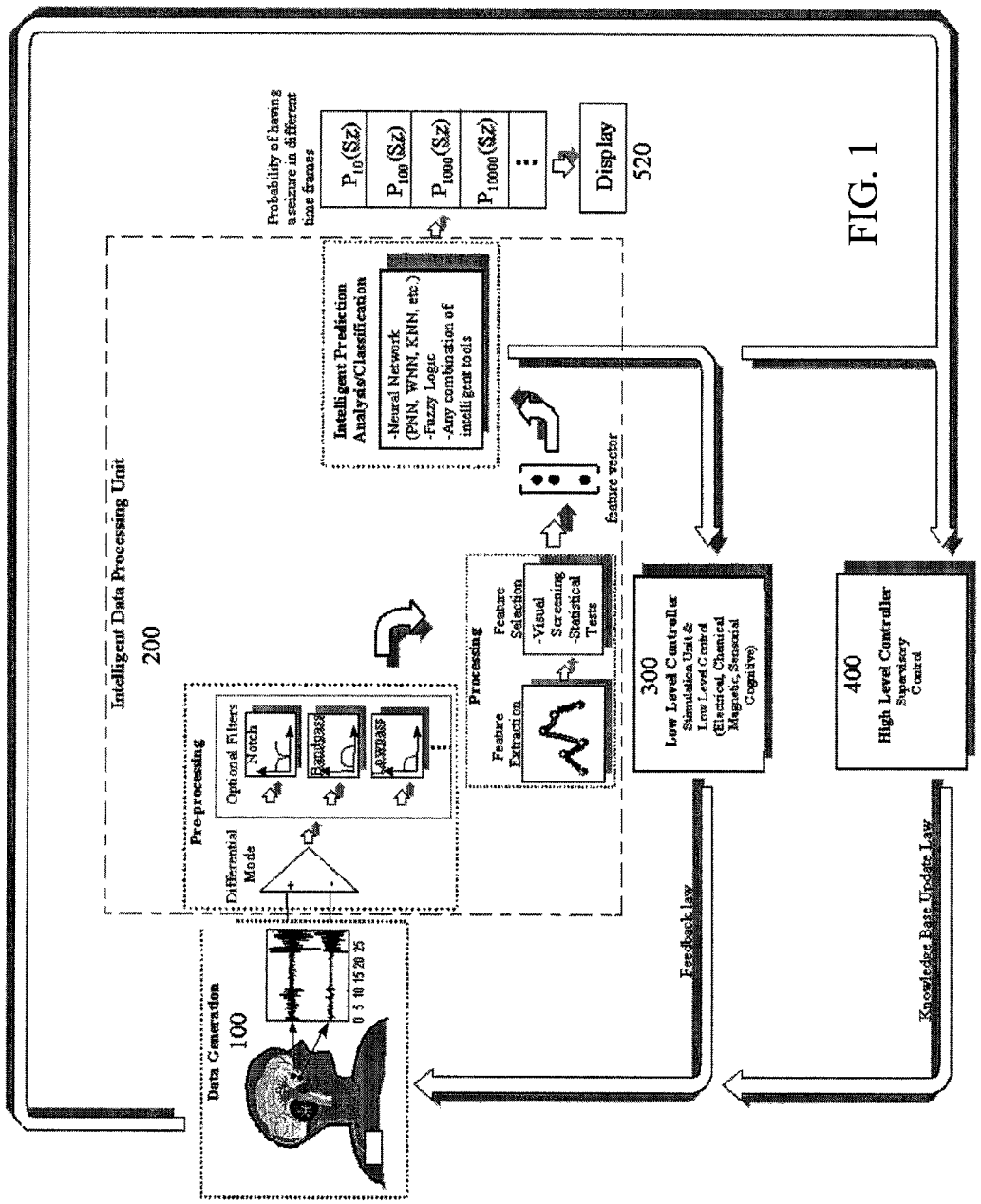
FIG. 1 illustrates an overview of the overall system architecture of the present invention.

The preferred embodiment of the invention uses brain electrical signals or other input signals and an implanted processor to predict and provide early detection of the electrographic onsets of brain events such as seizures in an on-line intelligent arrangement that facilitates a wide variety of options. FIG. 1 is an overview of the overall system architecture from the data input to the output signal indicating the probability of having a brain disturbance or seizure, and to the closed-loop controls included in the system. The data is sketched as brain electrical activity, but it is not restricted to this type of activity; it can also include chemical, magnetic, temperature, blood pressure, and/or any other physiological variable that can contain relevant information for prediction and early detection of the seizure onset. In FIG. 1, the main system blocks can be visualized starting at the data generation block 100, then the intelligent data processing unit 200 which is a key part of the system responsible for forecasting, and the low level and high level closed-loop controls 300 and 400, respectively that tie into a supervisory control approach. In this figure, the data generation block 100 does not include the brain, which is the plant in this case; rather it only includes the electrodes, cables, and any sensor used to capture physiological variables that go into the forecasting section or intelligent data processing unit 200. The system is implemented with both an off-line and on-line methodology. The off-line part of the method plays a role at the initialization stage, and after that, at subsequent adaptive parameter re-tunings, setpoint readjustments, and at a higher layer of hierarchy as a research tool seeking for an understanding of the mechanisms that operate during epileptic seizures or brain disturbances, and investigating new algorithms or features for prediction and early detection of the UEO of seizures.

Figure 2:
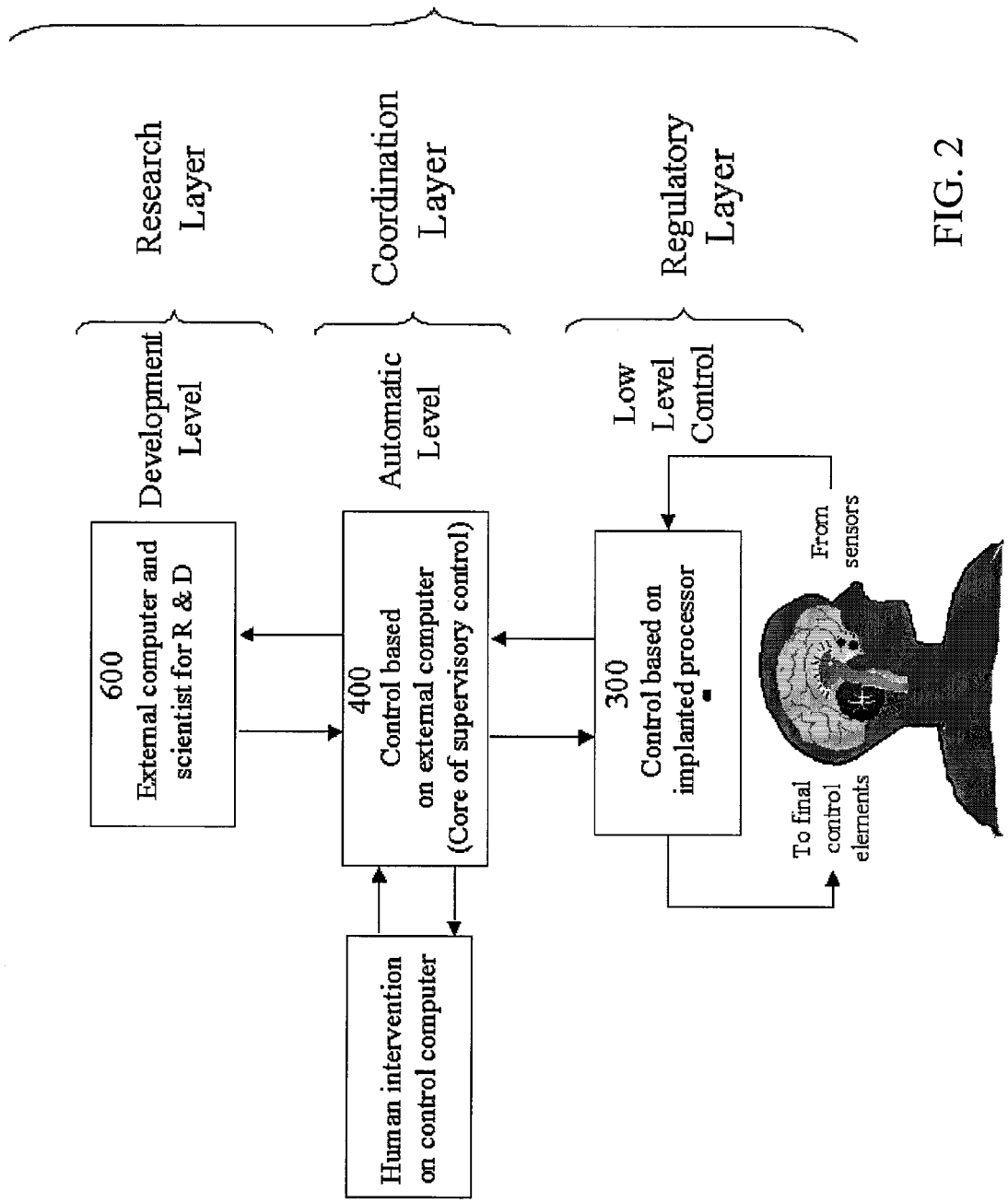
FIG. 2 illustrates an exemplary scheme of the multi-level supervisory control of the present invention.

FIG. 2 illustrates the scheme of the multi-level control, where the three layers of this control scheme are depicted. The control actions are performed through these layers organized in a hierarchical manner. The main goal of the multilevel control is to keep the patient from having seizures despite environmental and physiological load disturbances. To achieve this objective, a supervisory control is implemented providing (a) continuous regulation of the controlled variables, (b) adaptation to external or internal changes over time, and (c) a knowledge base used to accomplish the regulation and adaptation by incorporating information as it arises, and updating the system settings and parameters appropriately. At the regulatory layer, a low level supervisory control 300 takes care of the actuators (stimulation units) and determines and adjusts their settings in a continuous fashion. The control in this layer is based on the implanted processor. At the coordination layer, the high level of supervisory control 400 is achieved, based on an external computer where the knowledge base resides. This layer is responsible for re-tuning system parameters such as those related to fusion of sensory data, feature extraction, feature normalization, neural network retraining, fuzzy logic adjustments, fault diagnosis of actuators, sensors, implantable device, etc. This layer can operate in an automatic mode where a master program monitors the controlled variables and updates the control law accordingly; or in a semi-automatic mode where the doctor or specialist can input parameters directly into the system via the master program user interface. At the highest level is the research layer based on another external computer 600 whose major function is to serve as a research tool to investigate new more powerful algorithms for seizure or brain disturbances, UEO prediction and detection, new control strategies, other types of parameter adjustment, and also to analyze physiological mechanisms that can explain seizures and other brain disturbances. This layer gathers information coming from different patients forming a database for research and development.

At the initialization stage, during the off-line part of the method, the system is installed and the initial settings are determined for all the blocks indicated in FIG. 1. The on-line operation follows after all settings are adjusted according to the patient. Future generations of this invention might automate the off-line procedure, turning the apparatus into an almost completely on-line system with the exception of the electrodes positioning, the implantable device installation, and transference to the implantable device of newly developed and released algorithms (i.e., new features).

Figure 3:
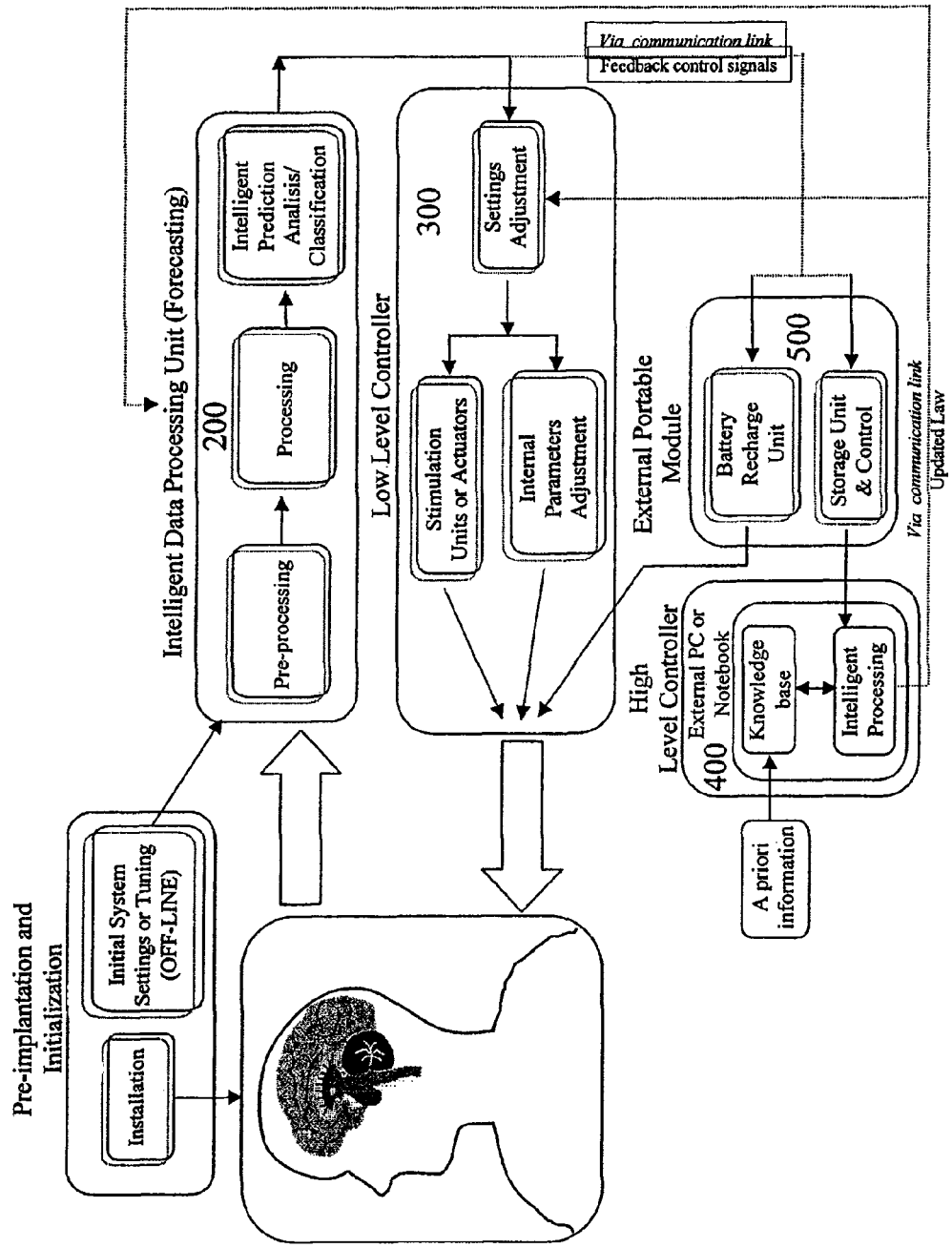
FIG. 3 illustrates the main stages and components of this invention in order to achieve the approach presented for an on-line implementation.

The initialization and operation of this apparatus is divided into three stages: pre-implantation and initialization, forecasting, and controlling. FIG. 3 provides an exemplary diagram illustrating the fundamental blocks that manage these stages. The stages are initiated consecutively and under different procedures. The first stage includes the installation and manual or automatic off-line tuning of the system. It has optional steps depending on the particular patient requirements, on the seizure complexity, and on whether the system is feature/parameter-tuned or only parameter-tuned. A feature/parameter tuned device refers to a system where the features are selected for each patient, depending on which features can capture the seizure UEO in advance. Therefore, different patients have different features within the feature vector, and once these features are selected their parameters are tuned. A parameter-tuned system uses the same features for all patients, and tunes the parameters of each feature on a patient basis. One common parameter that can be adjusted for all the features is the running window length used in the feature extraction.

Summarizing this idea, the embodiment of this invention is patient-tuned, with two possible alternatives. Either the same features are used for all patients and their parameters are tuned according to each patient, or the features are selected according to the patient and their parameters adjusted on a patient basis as well. The second approach is the more robust and is the system default.

An overview of the steps that comprise the initialization and operation of this apparatus is presented next. An exemplary general diagram of the stages and blocks involved in each stage is illustrated in FIG. 3.

1. First Stage: Implantation and Initialization

The patient undergoes a surgical procedure in order to accomplish the implantation and initialization stage. The following steps are used as part of the implantation procedure.

Step 1: Determination of focus region for correct installation of the implanted brain electrodes.

Step 2: Appropriate installation of the electrodes and other sensors. The sensors can be selected from the group of (a) intracranial electrodes; (b) epidural electrodes, such as bone screw electrodes; (c) scalp electrodes; (d) sphenoidal electrodes; (e) foramen ovale electrodes; (f) intravascular electrodes; (g) chemical sensors; (h) pupil dilation sensing systems; (i) eye movement sensors; (j) heart rate sensors; and (k) body temperature sensors.

Figure 4:
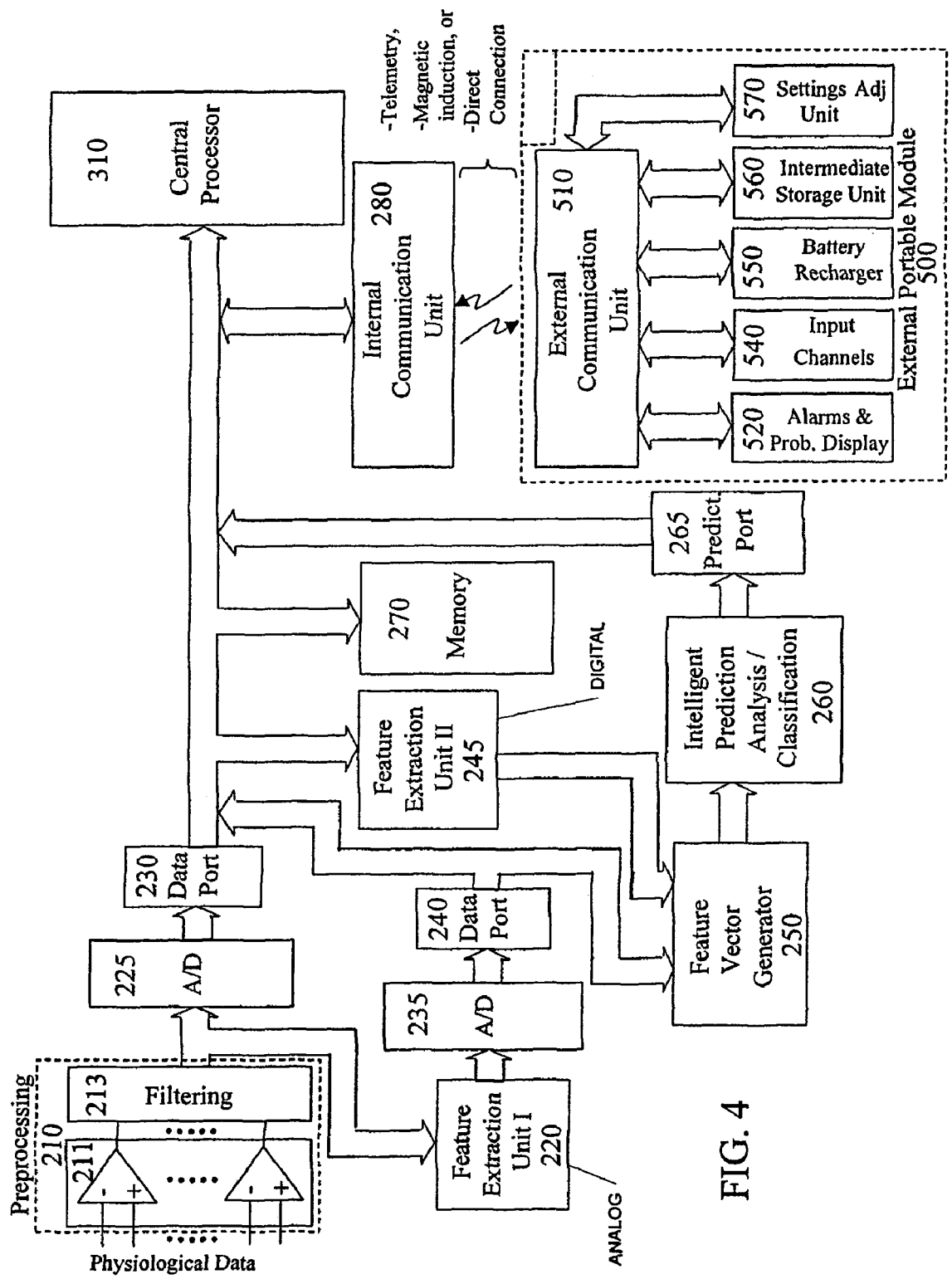
FIG. 4 illustrates an exemplary block diagram of the intelligent data processing unit that is the core section of the system and is mainly related to forecasting seizure or brain disturbances.

Step 3: Implantation of the electronic device into the brain. Once the implantation is completed, the initialization of the system is the next part of the implantation and initialization stage. In one embodiment of the invention, the initialization is performed by the implantable device in combination with an external PC or notebook or equivalently by the regulatory and the coordination layers, respectively. This is possible because the system has an optional external portable module 500 that contains an external communication unit 510, a settings adjustment unit with display and keypad 570, an intermediate storage device 560, a battery recharger 550, patient input channels 540, and data output channel 540 as shown in FIG. 4. The external communication unit 510 creates a data flow path from the internal communication unit 280 such that the data acquired by the implantable device, blocks 100, 200, and 300, is transferred to the intermediate storage device 560 within the external portable module 500. In this embodiment, at the initialization stage data must be collected to select and tune the features appropriately according to the patient. This implies that one or more brain disturbances or seizures must have been recorded to carry out the parameter tuning and/or feature selection. Therefore, the patient may walk out of the hospital with the external portable module 500 activated, while the system is still in the initialization stage and the forecasting has not started, and then return later for parameter tuning and/or feature selection. The recording time autonomy of the system depends on the final memory capacity achieved in the intermediate storage device, which can be based on a flash memory card that can store 160 Mbytes or more, or on any other type of memory device suitable for this portable module. Using a sampling rate of 200 Hz in the A/D converters and assuming an intermediate storage device of 140 Mbytes which may evolve into a higher capacity device as the technology advances, the portable module confers the equipment with a two-day recording time autonomy for two channels or more as new higher memory devices become available. This means the patient either has to be back in the hospital or have the system connected to an external PC at home every two days for data downloading from the intermediate storage device into that external PC, or into a remote PC that can be located at the doctor's office and where the information can be loaded via the Internet. In either case, the information is transferred onto the designated hard disk. An output signal is triggered by the external portable module before the intermediate storage device is full, reminding the patient that it is time for data downloading. If the patient does not download the data stored, then the intermediate storage device starts operating in a first in first out (FIFO) mode, such that once the download is accomplished only the last two days of data are available. With the continuous improvements in technology, the time between data downloadings can become longer as higher memory capacity devices are developed. When four or five brain episodes are recorded and downloaded into the high level controller, a feature selection process can then take place in the external PC or notebook if the feature/parameter approach is used, otherwise this step is skipped. The implantable device is based on a microprocessor, a digital signal processor (DSP), a field programmable gate array (FPGA), or an application specific integrated circuit (ASIC) processor 290, and the specific block of the implantable device that operates during the initialization is the intelligent data processing unit 200 whose major function is forecasting the brain event or seizure once the feature vector is established. FIG. 4 illustrates a diagram of the intelligent data processing unit 200. The initialization part can be split out in the following steps.

Step 4: Installation of the external portable module 500.

Step 5: Continuous data recording into the intermediate storage device 560 and downloading into the external PC or notebook 400 until around five or more brain disturbances or seizures are recorded. Ideally at least five brain disturbances should be recorded, however depending on the specific case, fewer or more brain disturbances may be required before proceeding with the next step.

Step 6: Sensor data preprocessing and fusion followed by feature extraction and selection at the high supervisory level in the external PC 400 where the data has been stored after downloading.

Step 7: Selection of the best feature set according to the procedure sketched in FIG. 5 by the coordination layer 400. The final product of this step is the establishment of the feature vector. This step can be skipped when the parameter-tuning approach is used.

Step 8: Transference and setting of the selected feature programs into the implantable device.

In this embodiment of the invention the feature/parameter approach is used, and therefore, the initial parameter tuning for each of the features selected and for the other system blocks is completed in the external PC or notebook 400. However, if the parameter-tuning approach is used in combination with the external portable module 500 for data recording, then either the external PC or notebook 400 or the implantable device processor performs the initial parameter tuning.

In another embodiment of the invention, a manual parameter tuning is accomplished by the doctor or authorized individual through the external portable module 500 via the settings adjustment unit 570, based on previous knowledge information of the patient, on historical information available from other patients, and on the specialist experience. In other embodiments of the invention, the initial parameter tuning is performed automatically by new generations of the implantable device based on the development of new devices and technology advancements.

To summarize, in the default embodiment of the invention, the initialization part of this stage is performed by the implantable device 200, 300 and by the external computer 400. The core of the supervisory control that resides in the external computer 400 located within the coordination layer can be assisted by a doctor or specialist to establish desired setpoints, so that the system parameters can be tuned properly for the patient.

2. Second Stage: Forecasting

The second stage is the system core, in which the forecasting takes place. FIG. 4 shows a block diagram of this stage. It encompasses the on-line implementation of the forecasting system 200, which includes components for pre-processing 210, analog to digital conversion 225, 235, real time analog and/or digital feature extraction or processing 245, 220, respectively, the feature vector generator 250, the intelligent prediction analysis/classification 260 for estimation of the probability of having a seizure within certain time frames and alerting when a seizure is approaching, the internal communication unit 280 and the external portable module 500. The closed-loop feedback control that resides in the implantable device is not activated at this point. A description of the sequential tasks performed in this stage follows.

Figure 6A:
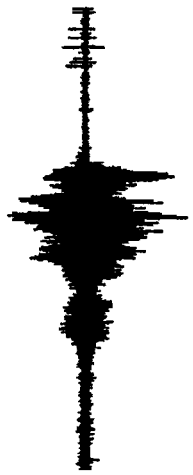
FIG. 6A illustrates the effect of subtracting the focus channel recorded with the intracranial EEG from its adjacent intracranial EEG channel for a 4-minute segment.
Figure 6B:
FIG. 6B illustrates the same 4-minute of IEEG depicted in FIG. 6A but without channel subtraction.

Step 1: Real time pre-processing of the input signals from different sensors. In the case of sensors capturing the brain electrical activity, typical preprocessing includes subtracting the focus channel signal from the adjacent channel and filtering when necessary (FIG. 1, block 200; FIG. 4, blocks 211, 213). FIGS. 6A-6B present the effects of adjacent channel subtraction on the IEEG signal. FIG. 6A presents a higher quality signal since a lot of artifacts present in FIG. 6B were abated by the subtraction. This is done to remove any noise common to both channels. As a result, any common mode cortically generated signals are also eliminated. However, this is not felt to affect adversely the seizure onset forecasting, since the seizure onset patterns are highly localized to the focus channel. IEEG data have been processed both with and without channel subtraction. Results by Esteller et al. ("Fractal dimension characterizes seizure onset in epileptic patients", ICASSP 1999) have demonstrated better detection and forecasting with channel subtraction for specific features. This shows that for those particular features the spatial separation between the electrodes inside the brain is short enough to cancel the common noise in that region, and long enough to capture a voltage difference between the focus and its adjacent electrode. Of note, each of these electrodes records the global activity of many thousands of neurons.

Step 2: Depending on the type of processing required by each particular feature, they are extracted either at an analog level (level I or 220) or at a digital level (level II or 245), whichever is more suitable for the specific feature considering computational requirements, hardware capacity, and time constraints. The analog level of feature extraction is indicated in block 220 of FIG. 4.

Step 3: Digitizing 225, 235 and recording 230, 240, 270 the preprocessed and processed sensor signals with optional downloading of the recorded data into the computer 400 or into the intermediate storage device 560.

Step 4: Extraction of the features at the digital level as indicated in block 245 of FIG. 4.

Step 5: Generation of the feature vector or feature vectors 250 if more than one time frame is used. Features extracted at levels I and II are combined following a running-window methodology. This methodology is utilized for the generation of the feature vector(s) as sketched in FIG. 7. For a pre-established window length, the features within the feature vector are computed. Subsequently, the window is shifted over the input signal or signals allowing some overlap and the feature is computed again. The feature sampling period is given by the shifting for which reasonable values are around half a second.

Step 6: The intelligent prediction analysis/classification can have an additional processor if the need arises and the processing time of the central processor 310 is not sufficient for the computations required by the implantable device. Before describing the intelligent prediction analysis/classification step 260, a feature normalization step is necessary. Typically the normalization involves subtracting the mean and dividing by the standard deviation. This is performed directly by the feature vector generator 250. Logically, the feature mean and standard deviation have to be estimated. The estimation of these parameters is conducted through a longer time window, which implies that a succession of feature vectors has to be generated and stored to estimate the values for these parameters. This procedure is performed by the implantable device, and more specifically by the central processor 310 or the additional processor if this is available. Once the parameters have been determined, the features are normalized appropriately. The parameters are updated as new feature values are computed in an on-line mode of operation, providing adaptability at this inner layer of the system. These parameters are also estimated by the high level supervisory control 400.

Step 7: Intelligent analysis of the feature vector, for each time frame considered, is performed through a fuzzy system or a neural network (NN) such as the probabilistic NN, the k-nearest neighbor, the wavelet NN or any combination of these, to provide an estimation of the probability of having a seizure for one or more time frames. This analysis is performed by the block denoted as intelligent prediction analysis/classification 260 illustrated in FIGS. 1, 4 and 8. The implanted processor 310 guides this analysis, however if an additional processor is used, this will take the leadership for this block. An in-depth presentation on how the probability of having a seizure is estimated can be found in U.S. Pat. No. 6,678,548, incorporated by reference in its entirety herein. The coordination layer of the supervisory control 400 must be connected periodically or as required or indicated by the doctor through the external portable module 500 with the goal of re-tuning the system parameters or adjusting the set points according to physiological and environmental changes. It is expected that as time progresses the actions required from the supervisory control will lessen, and therefore, the external connection to a PC, for further analysis and inspection of the system or for data recording may be needed rarely or occasionally. The ideal scenario is that the system reaches a steady-state equilibrium where brain episodes are prevented by the brain stimulations such that they do not occur at all, and a clear measure of this is given by the seizure frequency of the patient. Thus, a combination of this adaptive implantable device with a complex system like the brain should exhibit zero or very near zero seizure frequency to consider that it has reached the ideal equilibrium.

Step 8: The probability output of having a seizure for one or more time frames is shown on a portable display 520 contained within the external portable module 500. When this probability is higher than an adaptive threshold, a sound, visual, and/or tactile alarm(s) is(are) activated to alert the patient of the oncoming seizure. A more detailed description of this probability output and its operation is presented in U.S. Pat. No. 6,678,548.

Step 9: This step utilizes the external portable module 500 and the internal and external communication units 280, 510, respectively). The external portable module 500 has its own preprogrammed processor with specific tasks that include scheduling and control of data downloading into the intermediate storage device, data transference from the intermediate storage device to an external PC with the option of transference through the Internet, battery recharger, display and keypad, patient input channels, output channel with the alarm(s) that indicate the probability of having a seizure, external programming control or settings adjustment unit 570 whose function is the programming of the different options that the apparatus offers via the keypad, and data transference from the external PC to the external portable module to establish the supervisory control actions and communicate them to the implantable device. The settings adjustment unit 570 is password-activated such that it is protected and only authorized personnel can access it.

Step 10: The communication link is accomplished by a direct electrical connection, by telemetry, by magnetic induction, by optical or ultrasound connection as indicated in FIG. 4. In either case, internal and external bi-directional communication units 280, 510, respectively are used to manage the information transference between the central processor 310 within the implantable device and the external portable module 500. The implantable device and the external portable module processors can write or read the internal and external communication units 280, 510, respectively, any time that it is necessary. Every time the internal 280 or the external communication unit 510 receives information from the other end, it sends an interrupt to the processor within the implantable device or within the external portable module, respectively. Interrupt priorities are assigned according to the importance of the information transmitted.

Step 11: The system records input signals in several possible modalities. One modality records the physiological input signals during approximately one hour or more depending on the on-board memory capability 270 finally achieved in the implantable device. In this modality the recording starts some time before the probability threshold for approaching seizures is reached, by utilizing a set of buffers available for the task of temporarily storing the data. This modality is permanently activated and provides information to the internal adaptation loop of the low level controller when it is activated. A second modality utilizes the external portable module 500 and is activated upon connection of the module to the system. It has the option of recording continuously the input signals, the feature vector, and/or the controlled variables into the intermediate storage device 560 via the communication link. Depending on the data option selected, the recording time autonomy will change. It will be the longest when only the controlled variables are recorded, and the shortest when the input signals, the features, and the controlled variables are selected for recording. The external portable module 500 indicates when the intermediate storage device requires downloading of its stored data into an external PC representing the third storage modality. These downloading times are required to keep memory available in the intermediate storage device for incoming data. Three levels of data downloading are possible, one from the implantable device 200, 300 to the external portable device 500, and the others from the external portable device 500 to the external PC 400. The communication link for the first level of data downloading from the implantable device into the intermediate storage device is established by either a telemetry unit, a special hook up, magnetic induction, ultrasound or optical connection. The third storage modality has two options or levels of data downloading. One level of data downloading from the intermediate storage device to the external PC is established by a direct electrical connection in the form of a USB port, a serial port, or a parallel port. The information downloaded into the external PC is stored on a hard disk specific for this purpose. The second level of data downloading from the intermediate storage device to the external PC is accomplished through the Internet. In this form the information can be downloaded into a computer that can be at a different physical location, either at the doctor's office, laboratory, etc. The information recorded on that disk can be retrieved by the supervisory control at the coordination layer. At the automatic level of operation of the supervisory control, the information is retrieved by an intelligent master program that is running in the background; and at the semiautomatic level of operation, the information is retrieved by the doctor, the patient, or an authorized individual, via the software user interface that allows the interaction with the master program. Any of these recording modalities can be manually deactivated by the doctor or an authorized individual.

Step 12: Before proceeding with the activation of the implanted close-loop control (i.e., the starting step of the next stage), an adaptation time must be allowed for the forecasting block to reach a finer tuning. The time required for this initial adaptation procedure highly depends on the seizure frequency of the patient. At least five to ten seizures must have occurred after the forecasting is activated to warrant proper adjustment of this stage. The adaptation requires the use of the external portable module 500 for data recording and communication with the supervisory control. The initial adaptation is performed at periodically discrete times when the patient connects the external portable module 500 to the high level supervisory control 400, either as a direct connection to the computer where the master supervisory program that manages the high level control resides, or to another external device or computer that will transmit and receive information to and from the supervisory control computer via the Internet. The initial time spans between consecutive communications with the supervisory control may be around two days. After this initial adaptation/learning procedure the system can start the third stage or controlling stage, where the implantable close-loop control is activated. The adaptation will continue but at longer time spans that can be linked to a doctor or a specialist check-up appointment where the supervisory control re-tunes setpoints and readjusts parameters according to the most recent information archived in the knowledge base. Occasionally, the doctor or specialist can request at his discretion that the patient stores the data into the supervisory control at the coordination layer continuously for a week or the time they considered, or only at the specific times brain events or seizures occur, in which case, the patient is permanently wearing the external portable module, but he only downloads the data when a brain disturbance occurs, either a seizure, an aura, or any other brain event. In this form, the brain event and two days of consecutive data before the event occurred are stored in the intermediate storage device. This allows the master program and/or the specialist to reexamine the scenario, to consider new variables not observed previously, and to re-tune the system in a similar way that a car tune-up is conducted. This adaptation ability accounts for long-term physiological changes and for environmental changes, which assures the long lasting capacity of the apparatus. Furthermore, the highest layer (research layer) 600 allows the specialist to conduct innovative research and explore new horizons regarding brain events that can provide new evidence to explain the mechanisms that operate during these disturbances and brain diseases. In other words, this invention also acts as a research tool for the particular brain events that are being forecasted, without modifications to the apparatus or additional burden to the patient.

3. Third Stage: Controlling

The third stage is basically concerned with the control part of the system. It comprises a multi-level control illustrated in FIG. 2, that includes a regulatory (low level) control, a coordinating (high level) control, and a research (development level) layer from which modifications to the control laws in the lower layers can be derived. The high level control is provided by the supervisory control at the coordination layer that operates in two levels, i.e., an automatic and a semiautomatic level. The low level control is provided by a supervisory-regulatory control 300 that resides within the implantable device and whose main tasks are the internal parameter adjustments or tuning 320, and the brain feedback stimulation 330, 340 to avoid or mitigate seizures. The brain feedback stimulation is provided by the stimulation unit 340 shown in FIG. 8. In this figure, the outputs of the stimulation unit 340 (electrical, magnetic, chemical, sensorial or cognitive stimulation variables) are directly fed back into the brain, altering the net brain activity and becoming the manipulated variables 341-345. These manipulated variables are adjusted dynamically to keep the controlled variables at their set points or below the set points. The controlled or output variables, which quantify the performance or quality of the final product are the probability of having a seizure in one or more time frames and the overall system performance metric. The probability of having a seizure can be a vector if more than one time frame is used to estimate this probability. The stimulation block 340 can be manually deactivated by the doctor or an authorized individual. When this block is deactivated, the apparatus becomes a pure forecasting/warning device, which is the state it has at initialization. Two levels of stimulation are available in the stimulation block 340 depending on whether the control action or manipulated signal is activated by the patient or by the device. Stimulations at the patient level include sensory/perceptive and cognitive stimulations, and at the device level include electrical, chemical, magnetic, and certain types of sensory stimulation. This stage comprises the following steps.

Step 1: The low level supervisory control or implanted closed-loop control 300 is activated manually from the external portable module 500 or automatically via the high level supervisory control 400 through the external portable module.

Figure 20:
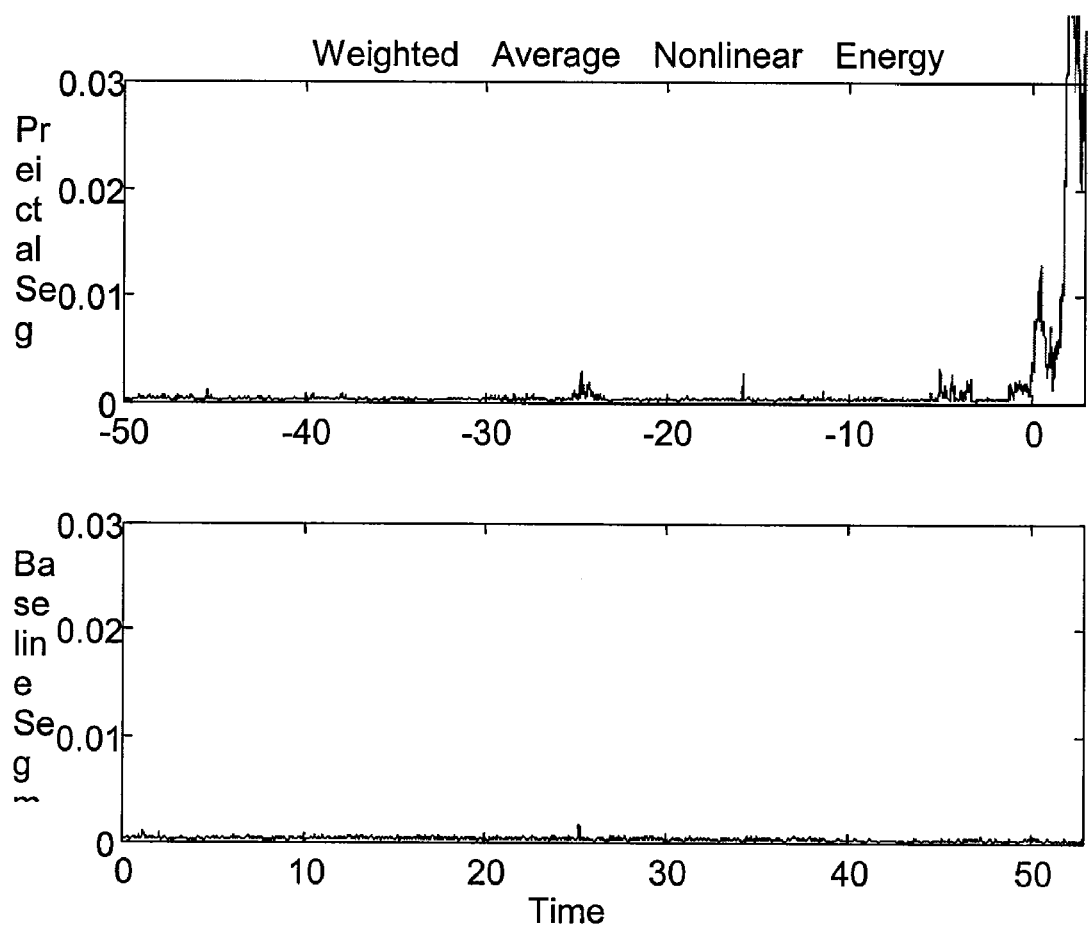
FIG. 20 illustrates a nonlinear energy derived feature for a preictal and a baseline record from another patient studied.

Step 2: The controlled variables given by the probability of having a seizure for one or more time frames and the overall system performance metric are used as control feedback signals by the low level controller to prevent seizures by producing an intermittent electrical, chemical and/or magnetic stimulation 341-343, or by instructing the patient to go into a previously specified sensory or cognitive procedure 344, 345. The duration, magnitude, type, and frequency of the electrical, chemical, or magnetic stimulation is adjusted to maintain the controlled variables at their set-points or range-points, as well as the duration, intensity, and type of sensory or cognitive stimulation. Prediction times on the order of minutes to an hour can be obtained with this invention (see FIGS. 15-17, 25-26), and in the worst cases on the order of seconds (FIG. 20). This represents ample time to avoid a seizure by releasing small quantities of a drug (chemical stimulation), by electrically stimulating focal points to ward off synchronized nerve impulses, by wearing a special helmet that provides a magnetic stimulation, by solving high cognitive problems, or by experimenting with sensory stimulation such as music, flavors, images, tactile sensations, or odors. The intensity as well as the level of invasiveness of the stimulus gradually increases with the probability of having a seizure. This multi-therapeutic approach is described in more detail in U.S. Pat. No. 6,678,548. However, a description of several invasive intervention measures is also described herein.

The intelligence structure of this invention is coupled to an array of interventions based upon electrical stimulation, chemical infusion and synthesis of artificial neuronal signals to counteract developing seizures as precursors build over time. The intensity of intervention, modality of therapy and spatial distribution of therapy are all adjusted as the probability of seizures increases over time. A guiding principle of these interventions is that the most benign forms of therapy are initiated relatively early in seizure generation and over a relatively small region of the brain, so as to cause little or minimal disruption of normal activity when the probability of seizure onset is relatively low. This will allow intervention to be triggered by prediction thresholds with high sensitivity (e.g., very low false negative rate) at the cost of a relatively low specificity (e.g., relatively high false positive rate). As the probability of seizures increases, therapeutic stimuli are increased in intensity, duration, frequency of delivery, and are delivered over a wider area of the brain. Since patterns of seizure precursors and their spread in space and time leading up to seizures are mapped and used to train the device on each individual patient, therapy is delivered over broader areas, just ahead of the anticipated region of spread, as seizure precursors develop, if they do not respond to earlier treatment. In this scheme, therapy can be delivered locally, in the region of onset, in a distribution surrounding the region of onset, isolating it from recruiting adjacent regions of the brain and spreading. Therapy can also be delivered locally and/or remotely in subcortical regions such as the thalamus, basal ganglia, or other deep nuclei and regions, escalating in intensity, type of stimulus and distribution of action, as seizures progress. This same principle is applied to therapeutic intervention if electrical seizure onset takes place, effecting treatment in the general region of onset, in deep brain structures which modulate the behavior of the seizure focus, or both simultaneously.

Interventions can include the following: (1) rhythmic electrical pacing, which changes in frequency, intensity and distribution as the probability of seizure onset reaches a threshold and increases; (2) chaos control pacing; (3) random electrical stimulation to interfere with developing coherence in activity in the region of and surrounding the epileptic focus; and (4) depolarization or hyperpolarization stimuli to silence or suppress activity in actively discharging regions or regions at risk for seizure spread. This activity can also be delivered to numerous electrode sites to create a type of "surround inhibition" to prevent progression of seizure precursors. These stimuli can also be delivered sequentially in a "wave" that sweeps over a region of tissue, so as to progressively inhibit normal or pathological neuronal function in a given region(s) or tissue, including cortical and subcortical regions.

The principle of altering and developing therapy in response to the changing probability of seizure, and/or the detection of specific events in seizure evolution, including electrical seizure onset and spread, is also applied to the delivery of chemical therapy. In this fashion, active therapeutic agents are infused or otherwise released in the brain regions where seizures are generated, or to where seizures may spread. As seizures become more likely, the amount, concentration or spatial distribution through which a chemical agent is delivered are all increased. As with electrical or other therapeutic interventions, patterns of delivery can include infusing a drug directly in the epileptic focus, in an area surrounding it, or to regions involved in early spread, or to more central or deep brain regions, which may modulate seizure propagation. These same therapeutic principles apply to distribution of maximal therapy when electrical seizure onset is detected, including distributing therapy to regions where seizures are known to spread and propagate. Last-minute treatment may include release of larger amounts of drug into the cerebrospinal fluid (CSF) space for circulation over wide regions of the brain or into the cerebral circulation. Other types of pharmacological agents may also be used in this scheme, such as agents which are activated by oxidative stress, which may themselves increase the concentration and distribution of an active therapeutic agent as seizure precursors evolve and the probability of seizures increases.

Therapy may also include delivery of stimuli, electrical, chemical or other, to peripheral or central nerves or blood vessels, in a graded fashion, as the probability of seizures increases, building up to therapy of maximal intensity at the detection of electrical seizure onset. Therapy may also include sensory stimulation (touch, temperature, visual, auditory etc.).

Finally, therapy may consist of synthesized, artificial neuronal signals delivered in such a way as to disrupt electrochemical traffic on the appropriate neuronal networks including or communicating with the ictal onset zone. Examples of such interventions might include transmission of synthesized signals which increase the output of specific cell populations, such as inhibitory interneurons, specific nuclear regions in the thalamus or other deep structures.

Using any or all of these methods singly, or in combination, therapy is directed toward preventing seizure onset, or isolating the development of seizures and their propagation so as to prevent or minimize clinical symptoms and the impact of these events.

Step 3: An evaluation is accomplished by the intelligent prediction analysis/classification block 260 within the intelligent data processing unit 200, to estimate the prediction performance, by measuring when possible, key parameters such as prediction time frame threshold error (PTFTE), false negatives (FNs), false positives (FPs), average prediction time achieved (APTA), seizure duration ($D_{Sz}$), etc. The PTFTE is directly quantified from the number of FPs and FNs. It can be measured only when either the controlling block 300 is deactivated (no low level control/no stimulation), or when it completely fails due to a general system failure, which implies that no electrical, chemical, magnetic, sensory, or cognitive stimulation is performed. When the stimulating system is deactivated, the apparatus is used for forecasting and not for controlling seizures. The prediction time frame threshold is the adaptive probability threshold used to declare an oncoming seizure for a particular time frame. In order to quantify a fault in the prediction time frame threshold, a measure of the achieved prediction time is needed, and therefore, the seizure UEO detection is required. The achieved prediction time is measured as the elapsed time between the moment the adaptive probability threshold that declares a seizure or brain disturbance is reached and the moment the UEO detection occurs. Among the several errors typically committed in this type of measurement, the biggest error in the achieved prediction time is due to the error in the UEO detection, but this error is within the range of seconds. Fortunately, the seizure UEO detection does not entail any additional circuitry or programming, since the prediction algorithms used to compute the feature vector also have the capability of seizure onset detection. The effects sensed and monitored through the selected features typically exhibit a more drastic variation as the seizure approaches, reaching their maximum change during the ictal period near to the UEO. This is logical and experiments conducted have proven that in most cases, the feature vector can be used efficiently for seizure prediction as well as seizure detection ("Accumulated Energy Is a State-Dependent Predictor of Seizures in Mesial Temporal Lobe Epilepsy," Proceedings of American Epilepsy Society, 1999, and "Fractal dimension characterizes seizure onset in epileptic patients," IEEE Int. Conf. on Acoustics, Speech, & Signal Proc., 1999). The probability of having a seizure is a continuously changing function of the time and the time frame under consideration $P_{TF}(Sz,t)$. If for a particular time frame (TF) considered, the probability of having a seizure $P_{TF}(Sz,t)$ reaches the adaptive probability threshold value $P_o$ that declares an approaching seizure, then a false positive (FP) is declared when a time identical to the TF under consideration has elapsed and no seizure has occurred, provided that the low level control is deactivated, and disregarding if there are oscillations of $P_{TF}(Sz,t)$ around $P_o$. Even if $P_{TF}(Sz,t)$ for that TF goes above the threshold and right immediately goes below, a FP must still be quantified. If $P_{TF}(Sz,t)$ is above the threshold during time $T_{up}$ longer than TF, then the number of consecutive and non-overlapping segments of TF duration that fits into $T_{up}+TF$ is equivalent to the total number of FPs that should be quantified for that TF. Note that rather than fitting these consecutive and non-overlapping segments of TF duration into $T_{up}$, they are fitted into $T_{up}+TF$ because the FPs are measured into this prediction framework such that the longer time $P_{TF}(SZ,t)$ is above $P_o$ without a seizure occurrence, the more FPs must be quantified. One FP is defined in the ideal case, when $P_{TF}(Sz,t)$ is above $P_o$ for an instant at time $t_o$, which mathematically will be described as a $P_{TF}(Sz,t)=\alpha\delta(t-t_o)$, where $\delta(t-t_o)$ is a delta function at time $t_o$ and $\alpha \geq P_o$; in this case, one FP is quantified. If $P_{TF}(Sz,t)=\alpha\Pi(t-t_o, t-t_o-T_{up})$, indicating that $P_{TF}(Sz,t)$ is a pulse of amplitude $\alpha$, such that $\alpha \geq P_o$, and duration $T_{up}$, such that $T_{up}=1.25$ TF then the number of FPs is quantified as 2.25. Considering the usual definition of a FP, it should be an integer number; however, the definition provided in this invention penalizes this type of error with more accuracy. Otherwise, $T_{up}=1.25$ TF and $T_{up}=0.65$ TF would yield the same integer number of FPs. If $P_{TF}(Sz,t)$ is again a pulse as mathematically described earlier, with amplitude $\alpha$, such that $\alpha \geq P_o$, and duration $T_{up}$, such that $T_{up}=1.25$ TF, but this time a seizure indeed occurred at time $t=t_o+t_1$ such that $t_o+t_1=1.1$ TF, then one FP has to be quantified even though the seizure occurred, because from the beginning of the pulse until time TF no seizure had occurred. FPs are quantified only when the controlling block is deactivated; otherwise, the activated control produces a stimulation to avoid the seizures or brain disturbances and the FPs will be unnoticed since they will be confused with avoided seizures. The FNs are quantified in three different ways. The first way occurs when the achieved prediction time as defined earlier is zero or less than one tenth of the time frame TF/10 for which $P_o$ is activated. The second way occurs when $P_{TF}(Sz,t)<P_o$, but a seizure occurrence is indicated by the patient through the patient input channel via the external portable module. The third way occurs when the supervisory control at the semiautomatic level indicates a seizure occurrence from direct inspection of the stored data by a specialist or doctor. The false negatives (FNs) are quantified over time to determine the prediction performance.

Step 4: The overall system performance metric is computed from the prediction performance and from the prevention performance. Along with the prediction performance, a prevention performance is determined by counting and storing the number of prediction-stimulations that were performed but failed to stop a seizure with respect to the total number of prediction-stimulations. This provides an indication of the failure and success rates of the stimulation block (lower level control) 340. In addition, the seizure frequency over time, the average seizure duration over time, the "aura" frequency over time, etc. are used to quantify the prevention performance. This is an important statistic since a reduction in the patient frequency of seizures after the device is implanted determines the apparatus performance. The overall apparatus performance is quantified in a metric that is a linear or a nonlinear combination of at least one of the performance measures assessed and is used in combination with the probability of having a seizure as feedback control signals. Also the system can utilize each of the measures that are used to compute the overall system performance (FPs if the stimulation unit is deactivated, FNs, patient seizure frequency, aura frequency, prediction-stimulation failures, total number of prediction-stimulations, $D_{Sz}$, APTA, etc.), or the prediction performance and the prevention performance as a feedback vector, rather than using the overall apparatus performance directly.

Step 5: The stimulation block 330 and 340, contained in the low level controller 300 receives as input, the control feedback signals or probability of having a seizure within one or more chosen time frames produced in the forecasting section as well as the different measures used to compute the prediction and prevention performances. The information contained in this feedback vector is used to adjust each of the stimulation block 340 parameters (intensity, duration, and frequency) and to determine the start time and the type of stimulation depending on the patient and on the seizure probability time frame activated and the probability value itself, and the type of stimulation within that kind, i.e., if a sensory stimulation of a visual kind is used, the types can be relaxing movie or picture, funny movie or picture, scary movie or picture, suspense, etc. Similarly, for each of the kinds of stimulations available 341-345. Note that the sensory/perceptive and cognitive kinds of stimulations have sub-kinds such as visual, auditory, tactile, smell, and taste, within the first category or kind; and reading, mathematical computation, and logic reasoning problems, within the cognitive kind.

Step 6: Initially, the feedback control law and the knowledge base update law are determined as a basic linear relationship between the variables that are fed back and the parameters that need to be adjusted according to the desired goal of a seizure-free patient with minimum invasion. Through the subsequent on-line tunings the parameters within the control laws, as well as the control laws themselves, will be updated as time progresses. Using intuition, logic, and previous available knowledge, mild interventions will be used first for longer TF. As the TF activated becomes smaller and/or the mild interventions do not decrease the probability of seizure, stronger interventions/stimulations have to be used. Mild interventions are the non-invasive kinds such as cognitive or sensory/perceptive stimulations. The duration of the mild stimulation or intervention $D_{st}$, will initially be proportional to the weighted average of the probabilities of having a seizure for each TF, where the weighting factor in each case is given by a stimulus factor. Mathematically, $D_{st}$ can be expressed as $$D_{st} = \frac{1}{N_{TF}} \sum_{TF} k_{st,TF} P_{TF}(Sz, t)/TF,$$

where NTF is the number of TFs utilized in the probability vector, and $k_{st,TF}$ is a specific stimulus factor initially determined as a function of previous available information such as the frequency of seizures, frequency of auras (if available), seizure duration, and type of seizure. Note that $k_{st,TF}$ depends on the TF and on the kind and type of stimulus used (st). Once the on-line operation is started and the controlling section is activated, this specific stimulus factor is updated using FNs, updated frequency of seizures, updated frequency of auras (if available), prediction-stimulation failures, total number of prediction-stimulations, $D_{Sz}$ achieved, APTA. The number of stimulation kinds available depends on the patient's evolution, initially all the stimulations proposed are used, but the adaptation procedure at all the control layers will progressively reduce and withdraw those stimulations with a high rate of failure. If more than one kind of stimulation is maintained, simultaneous stimulations can be applied as described more fully in U.S. Pat. No. 6,678,548. For stronger or invasive stimulations, a similar control law is used initially for each of the parameters required. For example, the electrical stimulation requires five parameters to be assessed. The intensity and duration are determined using the same expression for the duration of a mild intervention, the difference is in the specific stimulus factor that changes in each case. The other parameters are starting stimulation time, type of electrical wave to apply, and frequency (if there is a frequency associated with the type of waveform). The type of waveform is initially decided as a basic waveform that is easily generated and preferably with discrete values. In most cases, a pulse or half period of a square wave is used as the initial shape, but as the system gathers information from the patient, other waveforms can be tested if results are not satisfactory with the initial waveform. A similar criteria applies for the frequency of the waveform, initiating the control with a half wave per chosen duration. The starting stimulation time is determined by the time an adaptive probability threshold is reach by the actual probability of having a seizure for each specific TF. Each TF adaptive probability threshold is specific for each stimulus and is a function of the FNs, updated frequency of seizures, updated frequency of auras (if available), prediction-stimulation failures, total number of prediction-stimulations, $D_{Sz}$ achieved, type of seizure, and APTA.

Step 7: Relying on the research and coordination layers of the supervisory control 600 and 400 respectively, it is expected that the control laws will adapt to internal and external changes and evolve over time to accomplish the desired optimal equilibrium point where the seizure frequency reaches zero with less invasive and minimal stimulation, such as sensory/perceptive and cognitive. However, there are still many obscure issues regarding how the stimulations influence the patient. As the research and coordination layers (FIG. 2) update the incoming information, the interaction of the doctor, specialist and/or scientist with these two layers progresses, and the development level 600 (FIG. 2) provides enhanced control schemes to the lower layers, the equipment performance is enhanced over time.

Figure 8:
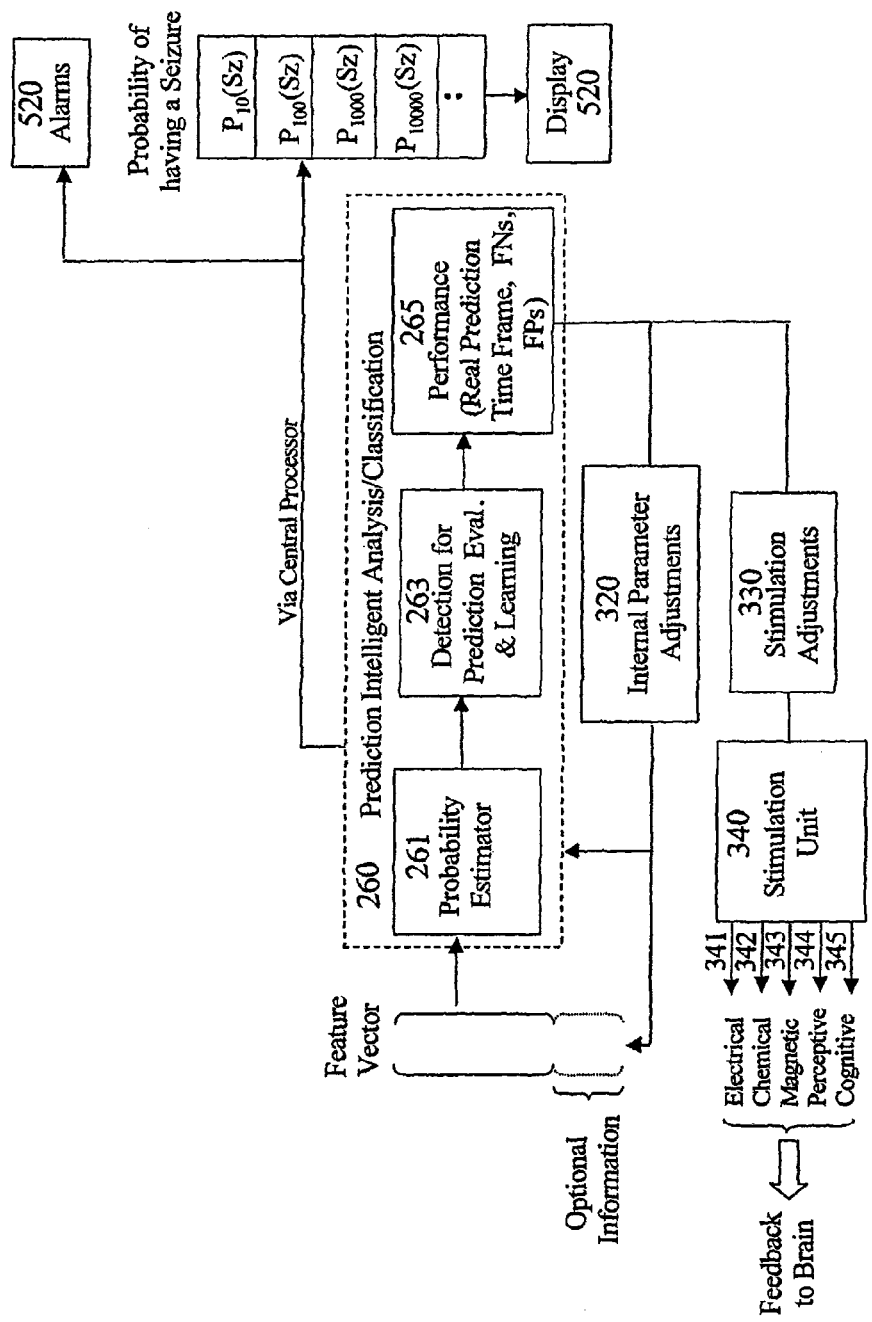
FIG. 8 illustrates an exemplary scheme followed by the low-level feedback control.
Figure 9:
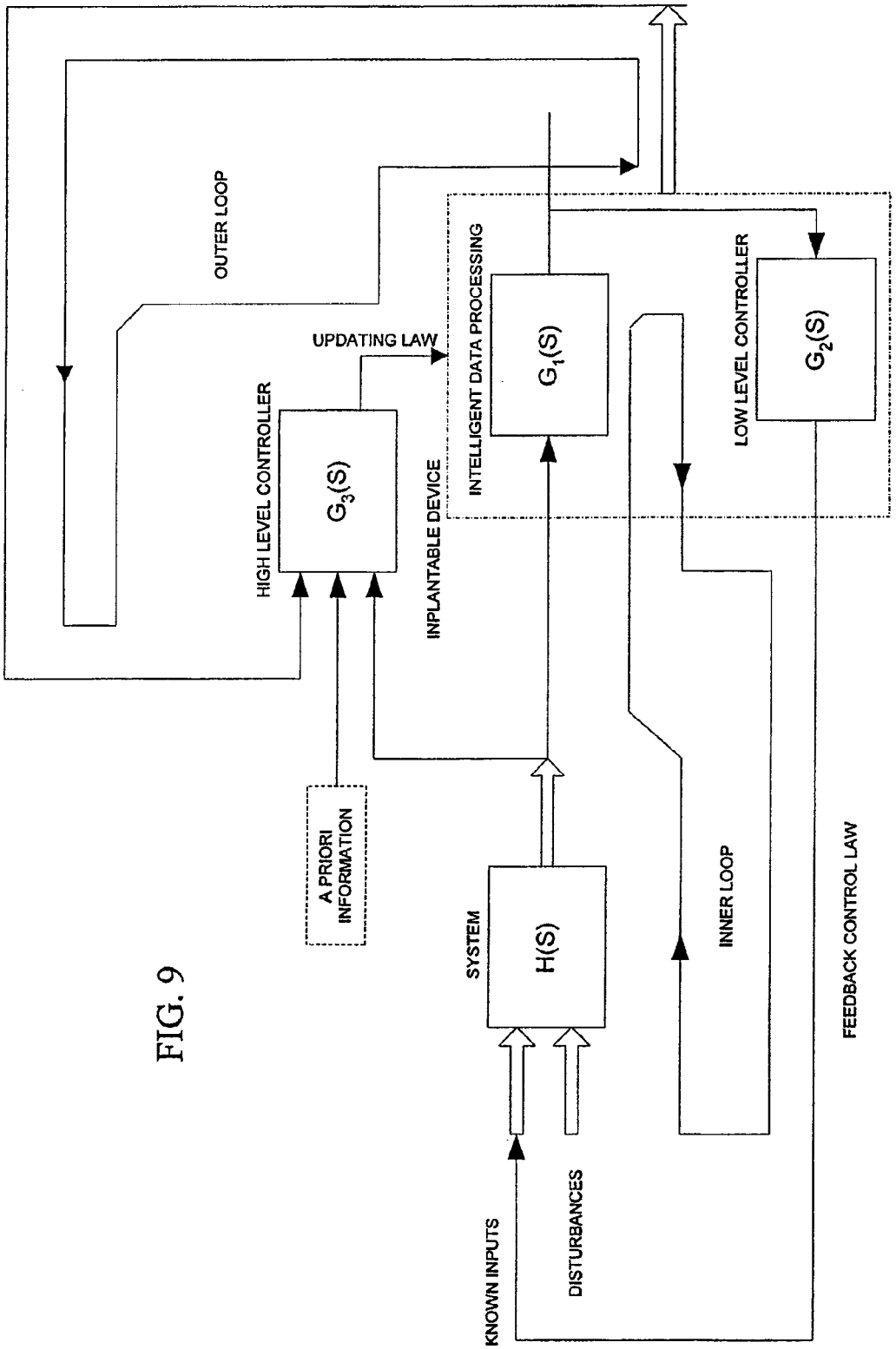
FIG. 9 illustrates a block diagram demarking the blocks within the implantable device and each of the processing or control blocks and the system, which in this case is the brain or the human body.
Figure 10:
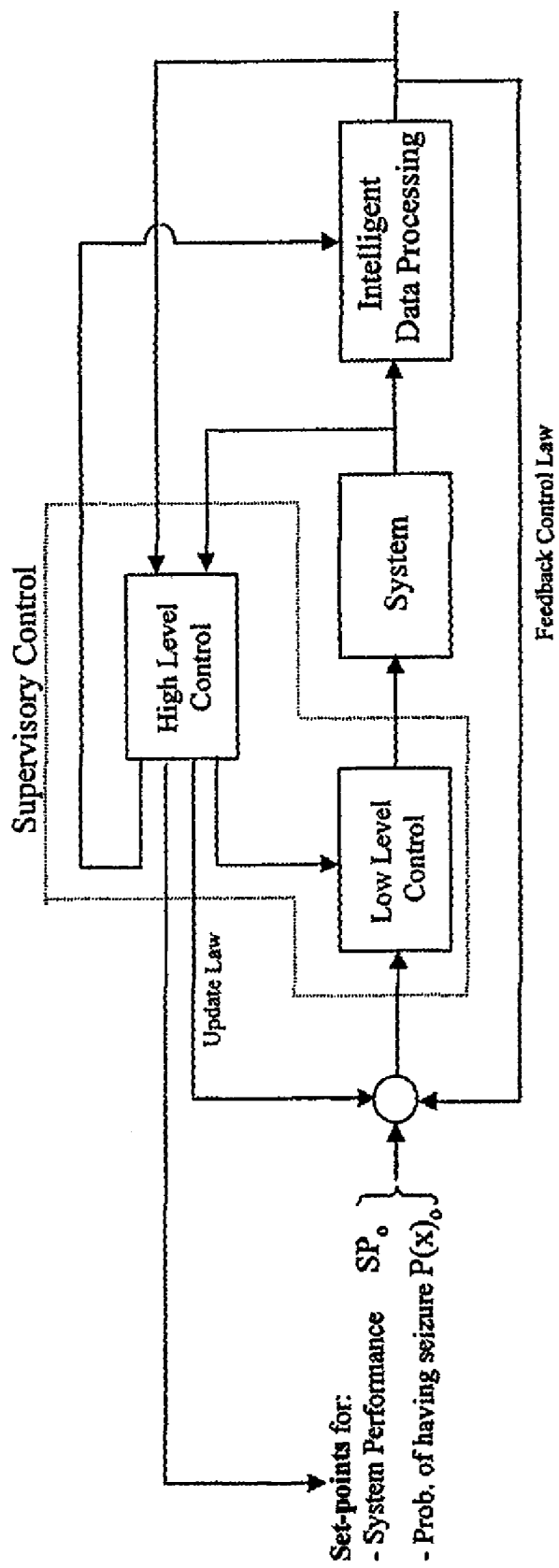
FIG. 10 illustrates a block diagram of the control mechanisms of the present invention.
Figure 11:
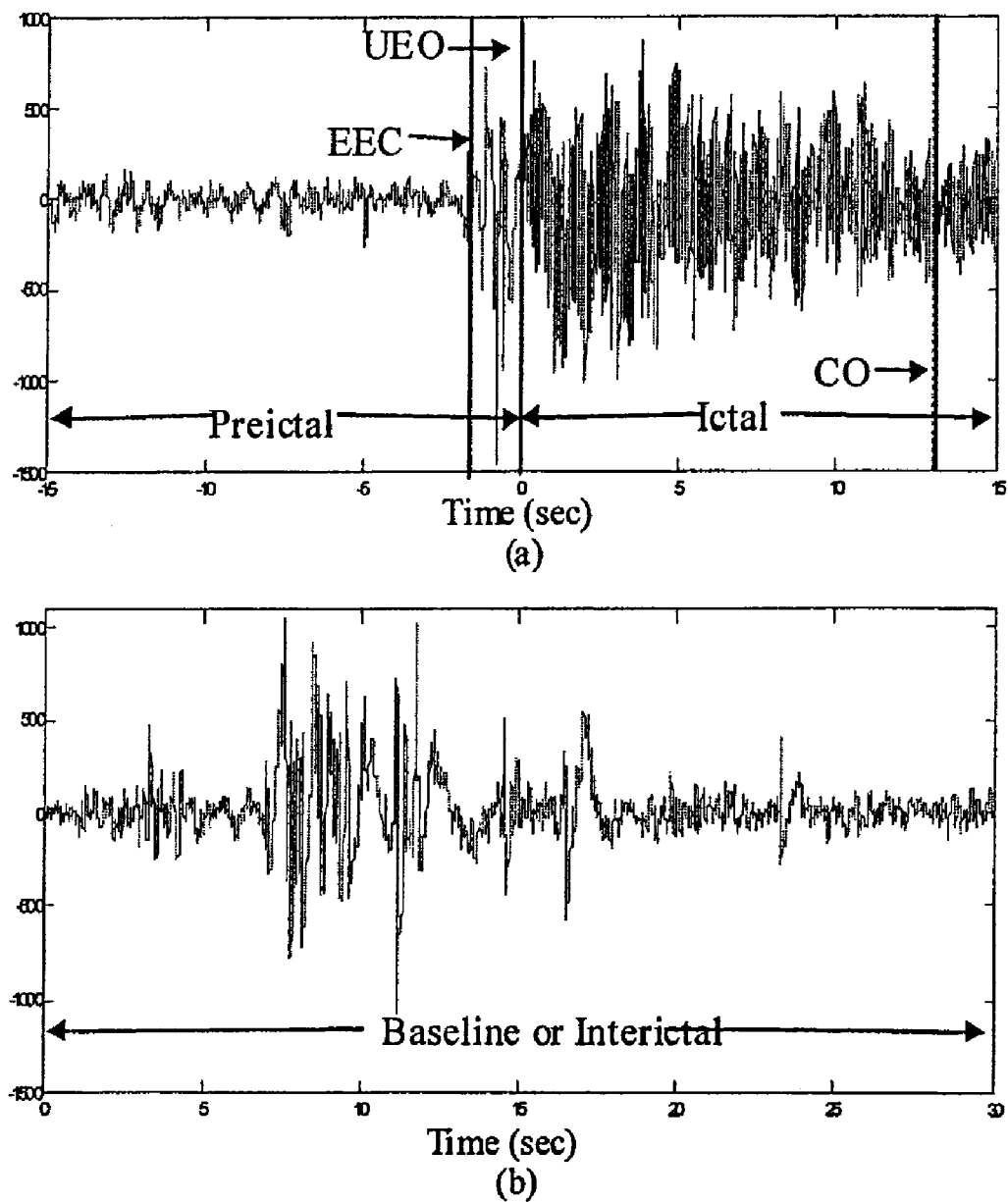
FIG. 11 illustrates segments of intracranial EEG that are useful to explain some terminology used throughout this description.

Step 8: Subsequent adaptive tunings of the internal system feature parameters, additional features (in case they are available), and analysis/classification parameters are performed in this step, based on the combined information of the control feedback signal and the overall performance measures achieved by the system (FIGS. 8, 9, and 10).

Step 9: The device has the option of reading information introduced by the patient by using the external portable module via the communication link shown in FIG. 4. The patient input channels 540 can be activated via the keypad, allowing the entrance of important patient information through different channels designated for each specific task. When information supplied by the patient is available, it is incorporated as an additional feature into the feature vector. In this form, the patient can provide additional information to the system through these channels. When he feels an aura he can press a button; when he or an individual observing him considers that a seizure is occurring, another button or combination of buttons can be pressed. The patient input channels 540 can be activated or deactivated directly in the external portable module 500, as well as many other options that the system offers.

Step 10: When the input channel of the external portable module 500 that provides the information regarding the patient aura sensation is activated, the system automatically adjusts itself to consider the new available information for the seizure probability assessment, according to pre-programmed parameters adjusted to each individual patient automatically by the control feedback signals, or manually by the doctor or expert.

Step 11: If the channel of the external communication unit 510 receiving the information regarding the occurrence of a seizure is activated, then this information is used in conjunction with the preictal and ictal data recorded to evaluate the system prediction performance. Among others the false positives, false negatives, and prediction times are used to assess the system performance.

Step 12: The system performance evaluation is always an option that can be activated by an authorized person. Two different system performance evaluations are accomplished automatically. One at the regulatory feedback control level and the other at the supervisory control level.

Another embodiment of the invention includes using other input signals in the system such as blood pressure, heart rate, body temperature, level of certain chemical substances in important organs, dilation of pupils, eye movements, and other significant physiological measures.

System Processing

The present invention delineates a patient-specific systematic approach for seizure prediction or early detection of UEO. The methodology followed is a typical approach used in artificial intelligence and pattern recognition. But in this invention, these methods are applied to the computational neuroscience field with adaptations to the specific conditions of the brain event or seizure prediction/detection problem, the detection as a consequence of the prediction and for performance evaluation purposes.

FIG. 1 depicts the architecture on which this invention is based. As can be observed in this figure, once the data is generated, a preprocessing stage is required to reduce the noise and enhance the signal for better class discrimination with minimum distortion and for appropriate data fusion. The preprocessed and fused data goes into the processing block, where the feature extraction and selection is performed. After appropriate features have been extracted and selected (optimized), an intelligent tool such as a neural network, fuzzy logic, or a combination of both achieves the intelligent prediction classification/analysis. Following this, a closed-loop control is activated and driven by the probability of having a seizure and by the overall system performance measures.

Figure 5:
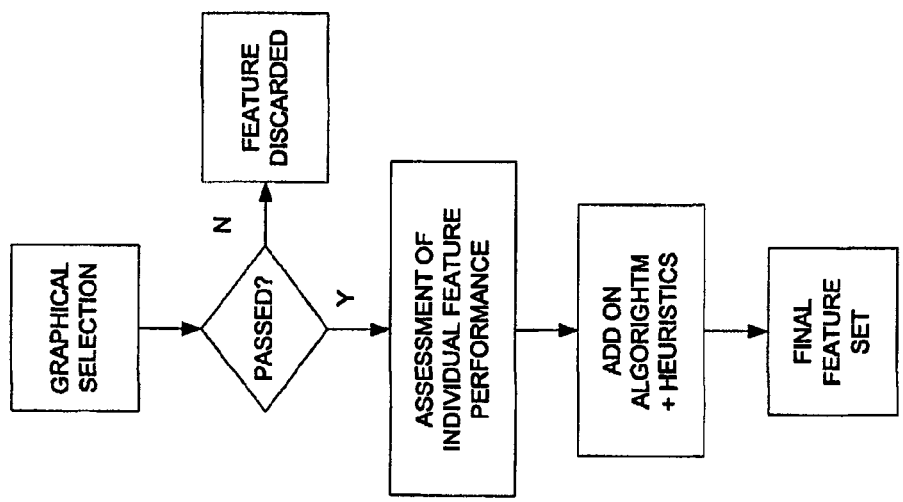
FIG. 5 illustrates the processing logic for the selection of an optimal feature vector.

In prediction/detection problems the feature extraction and selection is considered to be the key aspect necessary to achieve a correct classification and usually is the most critical. The intelligent prediction analysis/classification possesses a general and well defined operation once an effective set of features is found (see U.S. Pat. No. 6,678,548), but there is no straightforward procedure for determining the best set of features. However, FIG. 5 presents a flow chart with the procedure used in this invention for the selection of the best-feature vector.

Feature Extraction

Figure 7:
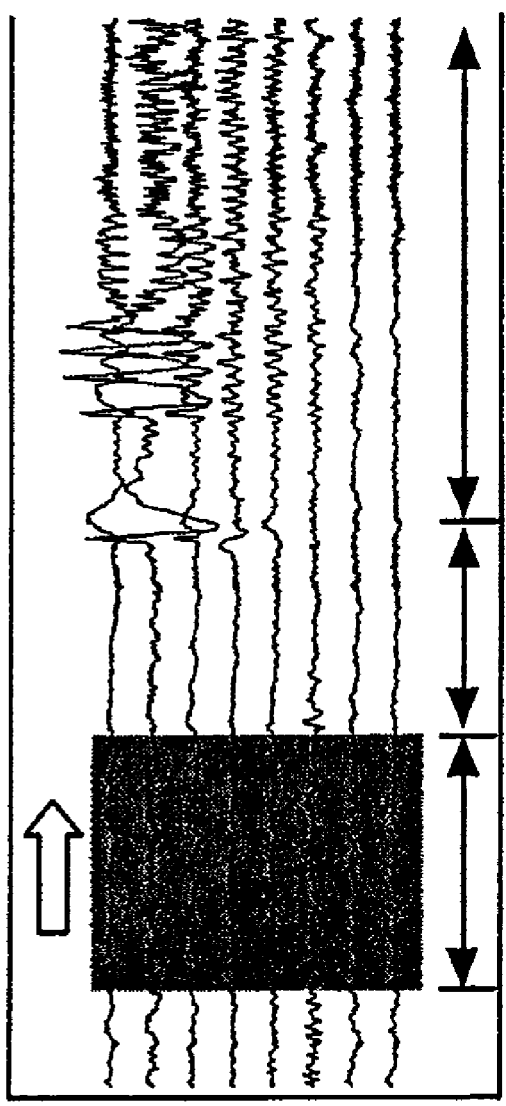
FIG. 7 illustrates the sliding observation window (gray area) that can include one or more brain signal (IEEG) channels as it is approaching an epileptic seizure.

The feature extraction is performed through a running window method, as illustrated in FIG. 7. The shaded area is the sliding observation window, which moves through the data as the features are computed. The data points inside this sliding window are used for feature generation as the window moves through the data. Therefore, this observation window is continually collapsed into a feature vector by means of formulas and algorithms that take preprocessed and fused input signals and produce scalar quantities as outputs, which then become the components of the feature vector.

Figure 12:
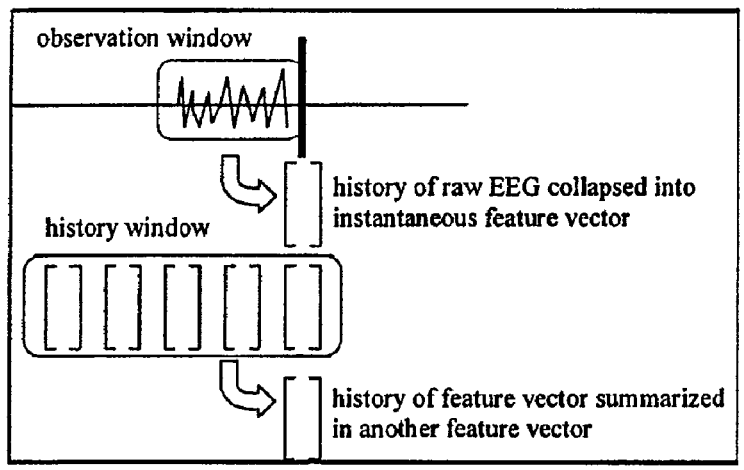
FIG. 12 illustrates the classification of the features into two types: instantaneous and historical features.

A feature library consisting of a large set of candidate features has been developed for feature extraction and selection. When following the feature parameter-tuned approach, an initial pre-selection of the features to be extracted is performed, guided by a combination of knowledge characteristics, intuition, and brainstorming. Once a large group of features is pre-selected, the features are computed. Two levels of features are defined at this point: instantaneous features and historical features, which are sketched in FIG. 12. The instantaneous or historical features can be limited to the focus region or can be derived, as a spatial feature arising from the combination of different regions within the brain, and not restricted to the focal area.

Instantaneous features are computed directly from the preprocessed and fused input signals through a running observation window. Historical features are "features of features" that require a second level of feature extraction, which entails the historical evolution of features through time. From this large set of instantaneous and historical features that are extracted (i.e., candidate features), the feature selection takes place.

The feature library developed contains more than 20 features. It includes a collection of custom routines to compute the features. Features from different areas or domains are extracted to explore a wide spectrum of possibilities. Among the domains analyzed are time, frequency, wavelet, fractal geometry, stochastic analysis, statistics, information theory, etc. In the following, a description of the algorithms, assumptions, and mathematical formulation for determining these features is presented in combination with some of the results.

Time Domain Features

The power, power derivative, fourth-power indicator (FPI), and accumulated energy (AE) are amplitude-based features. The nonlinear energy, thresholded nonlinear energy and duration of the thresholded nonlinear energy are based on an AM-FM demodulation idea first introduced by P. Maragos, et al. ("On Amplitude and Frequency Demodulation Using Energy Operators", IEEE Trans. on Signal Processing, vol. 41, No. 4, pp. 1532-50). Their calculations are provided below.

Average Power or Moving Average Power

Let the sequence $x(n)$ be a preprocessed and fused input signal, then the instantaneous power of $x(n)$ is given by $x^2(n)$. Considering that a sliding window is used, the power of the signal becomes the average power over the window mathematically defined as, $$P[n] = \frac{1}{N_1} \sum_{i=(n-1)N_1+1}^{nN_1} x(i)^2,$$

where:

$N_1$ is the size of the sliding window expressed in number of points, and n is the set 1, 2, 3, . . . .

The moving average of the power defined above is with zero overlap. If an overlap of D points is allowed, then the average power becomes:

$$P_D[n] = \frac{1}{N_1} \sum_{i=1+(n-1)(N_1-D)}^{n(N_1-D)+D} x(i)^2,$$

where:

$P_D$ is the average power or moving average of the power with D points of overlap.

Figure 13:
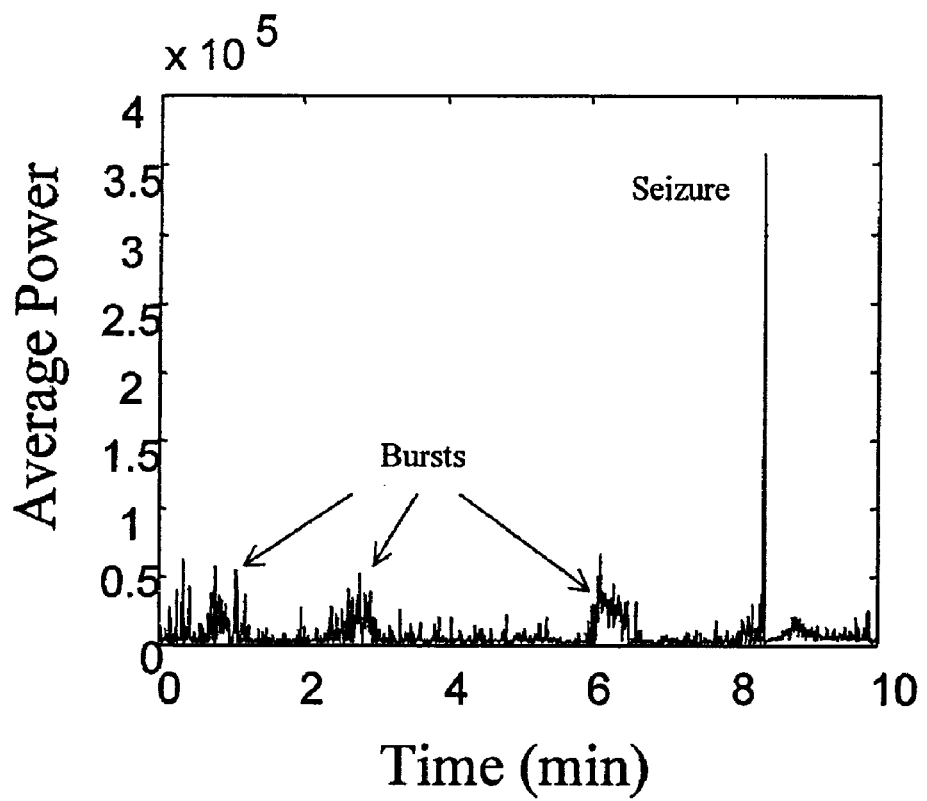
FIG. 13 illustrates the average power for both a preictal and an interictal segment in two one-hour records of an IEEG segment.

FIG. 13 illustrates the average power for one seizure record from an epileptic patient. Similar results were found in another patients. This feature was obtained using a window length of 1.25 sec. or equivalently 250 points with an overlap of 0.45 sec. (90 points); however, these parameters can be changed or adjusted to the patient.

Derivative of Power

The subtraction of consecutive samples of $P_D(n)$ corresponds to a discrete derivative of the average power, which can be expressed as $$\Delta P[n] = P_D[n] - P_D[n-1].$$

Accumulated Energy (AE)

The AE contains historical information and represents a discrete integral of the power moving average over time. From the power records obtained from the expression for $P_D[n]$, a new moving average window of $N_2$=10 points or any other value determined to be suitable for the particular patient, is slid through the power record with a 50% overlap or equivalently Da=5 points, and a new sequence is derived as the cumulative sum of these values. The following equation summarizes the mathematical computation of the accumulated energy or integral of the power for the specified band of time:

$$AE[k] = \frac{1}{N_2}\left[\sum_{j=1+(k-1)(N_2-D_a)}^{k(N_2-D_a)+D_a} P_D[j]\right] + AE[k-1].$$

Figure 14:
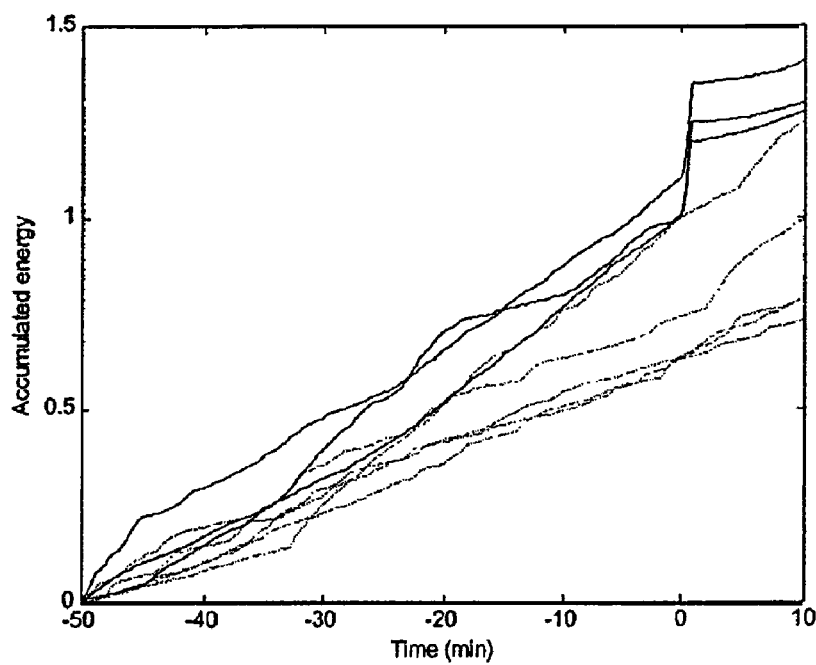
FIG. 14 illustrates the accumulated energy for the awake record of a patient. Note that preictal (continuous lines) as well as baseline records (dotted lines) are included in the plots to emphasize the distinguishability and prediction potential of this feature.
Figure 15:
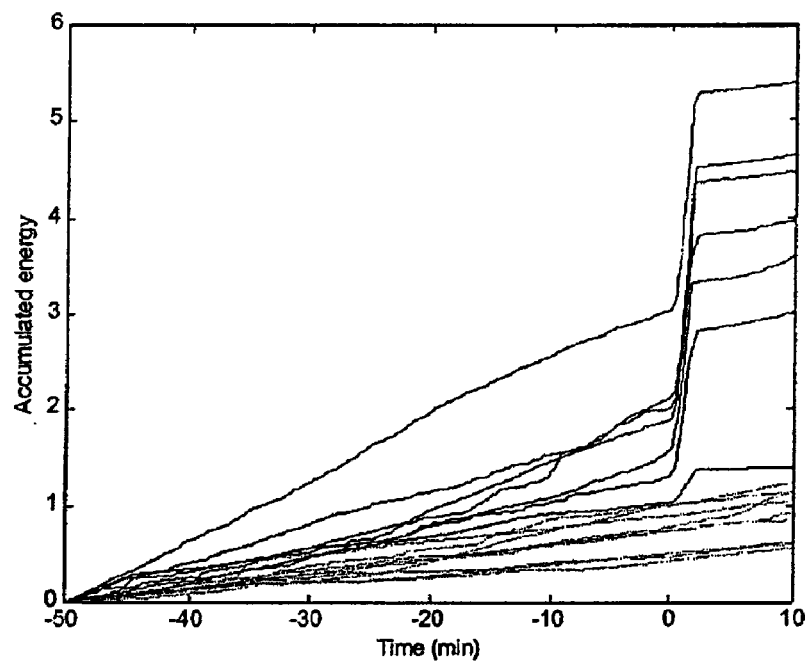
FIG. 15 illustrates the accumulated energy for the asleep record of a patient.
Figure 16:
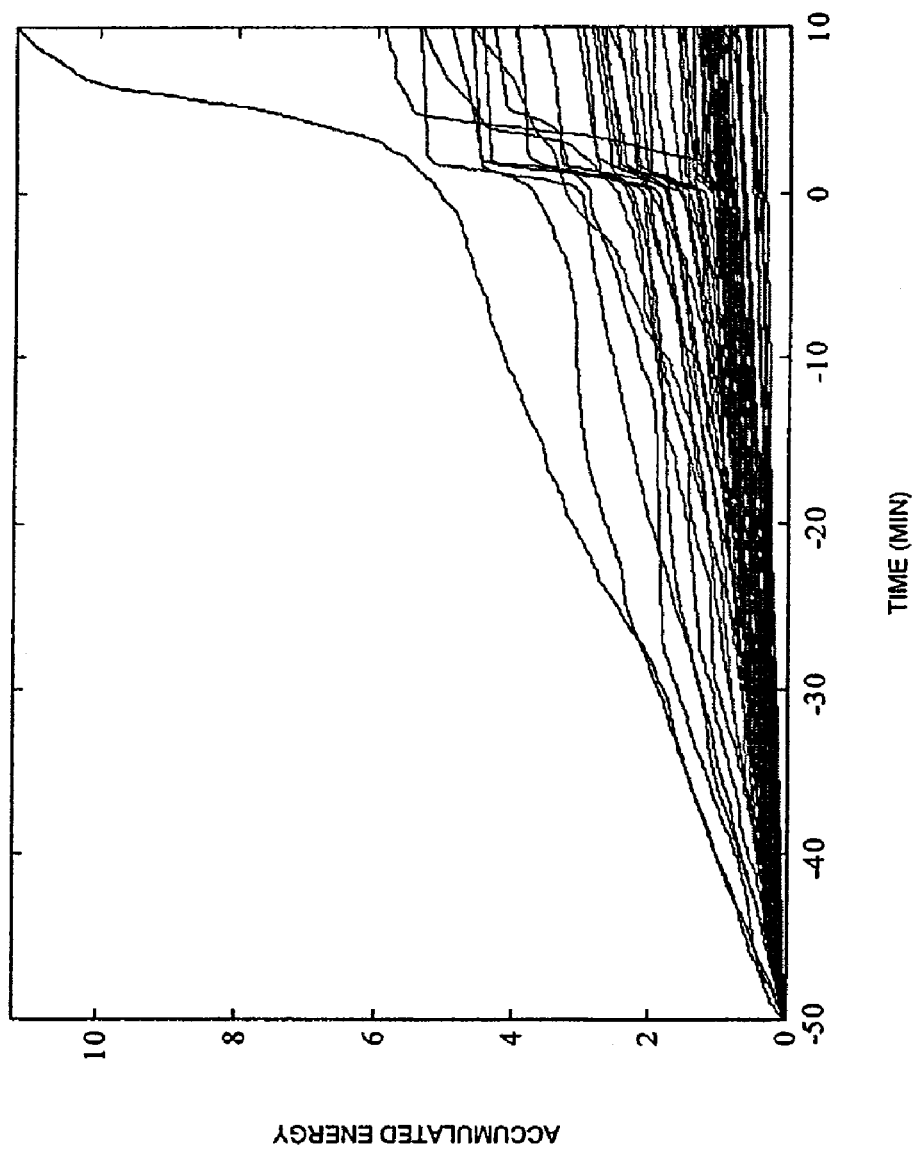
FIG. 16 illustrates the accumulated energy trajectories of 80 one-hour records including 50 baselines and 30 preictal segments.

This feature shows promising results for seizure prediction of UEO, as can be seen from FIGS. 14, 15, and 16. These figures present the accumulated energies for several one-hour records of IEEG as if they had occurred at the same time (same time axis), but this is just a way to compare the behavior of one-hour baseline and pre-seizure records from different time moments. Note that the time labeled zero corresponds to the UEO and the horizontal scale is in minutes. FIG. 14 illustrates the AE trajectories for all the awake IEEG records from an epileptic patient. The continuous lines of higher final amplitude correspond to seizure records, and the dotted lines of lower ending amplitude correspond to baseline records. A clear separability between the seizure and baselines records is observed from around 18 minutes before the UEO in most of the records. FIG. 15 shows the AE trajectories after a normalization. The one-hour IEEG segments in this figure correspond again to seizure and baseline records, but this time from both states awake and asleep. The normalization performed on the AE trajectories allows comparison of awake and asleep records within the same reference. Again in this figure the preictal segments exhibit higher AE than the baseline segments. Except for the lowest amplitude AE seizure record, a clear separation can be noticed around 20 minutes before the UEO. FIG. 16 illustrates the normalized AE trajectories for 80 one-hour segments from five different patients. It is clear from this figure that the seizure AE trajectories are concentrated at the top of the baseline AE trajectories. The observed behavior is similar in other patients. The normalization factor used over the AE was tuned for each patient according to an off-line procedure. The magnitudes of the non-normalized AE trajectories were always higher in asleep records than in awake records, and also changed from one patient to another. However, after the normalization, the AE trajectories became within the same range of values, preserving the relative differences within each patient.

Fourth-Power Indicator

Figure 17:
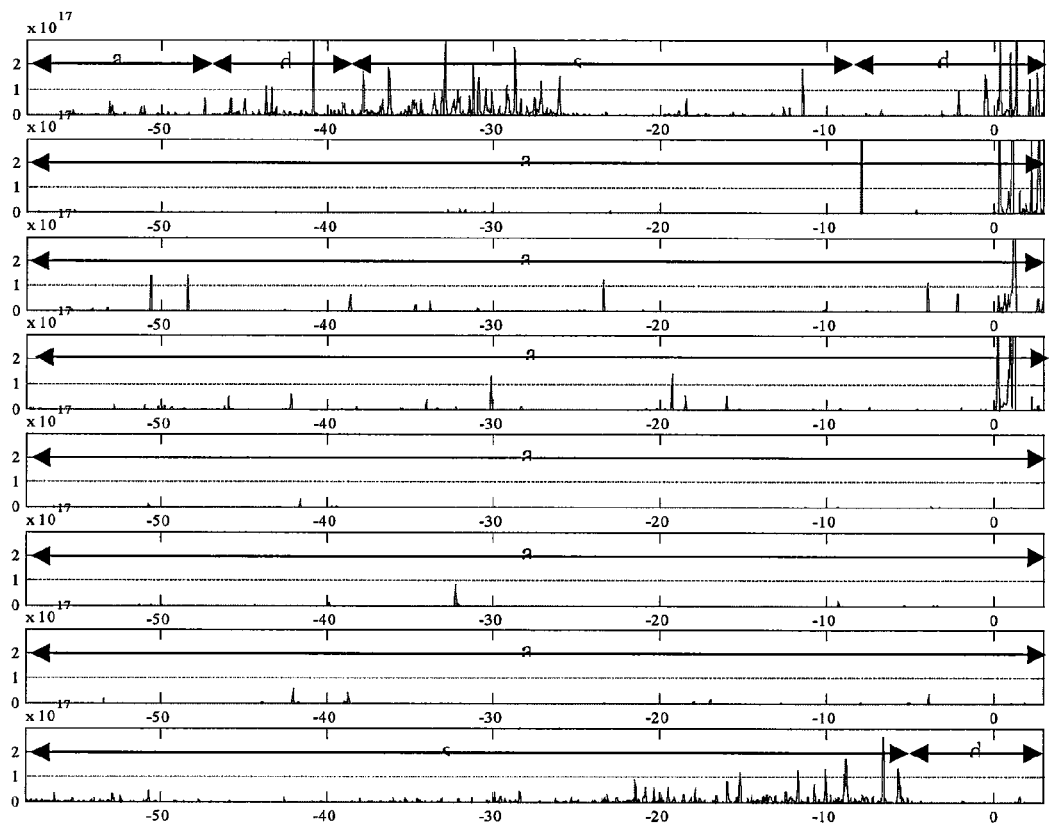
FIG. 17 illustrates the fourth power indicator (FPI) over time.

The fourth power of the time series $\Delta P[n]$ is computed over a second sliding window to accentuate the activity of higher-amplitude epochs in the preprocessed and fused inputs, sufficiently more than the activity of lower-amplitude epochs. The fourth-power indicator (FPI) is then given by, $$FPI(n) = \frac{1}{N_2} \sum_{i=n-N_2+1}^{n} \Delta P(i)^4,$$

where N2 is the size of the new sliding window over the time series $\Delta P[n]$. This second sliding window is chosen equal to 10 points, but can be another value. FIG. 17 shows the FPI in one of the patients analyzed. The prediction ability of this feature can be noticed in this figure. In this figure, the FPI from four preictal and four interictal IEEG segments is shown from top to bottom respectively. The dotted horizontal line on each plot represents a hypothetical threshold that when surpassed is considered as an indication of pre-seizure stage. The lines with arrows are used to point out the sleep-awake cycles (sac), the letters in the graph have the following meaning: a stands for awake, d for drowsy, and s for asleep. There are moments during the first four preictal segments when the hypothetical threshold is surpassed suggesting a relationship between this feature and the oncoming seizure event. Only one baseline record yields false alarms (the bottom one).

Average Nonlinear Energy or Moving Average Nonlinear Energy

The nonlinear energy (NE) operator arises in the area of signal processing and communications. It was first proposed by Maragos et al. ("On Amplitude and Frequency Demodulation Using Energy Operators", IEEE Trans. on Signal Processing, vol. 41, no. 4, pp. 1532-1550) as an AM-FM demodulator and later applied as a spike detector. The square root of the NE operator was shown to approximately track the product of the amplitude envelope and the instantaneous frequency of sine wave signals with time-varying amplitude and frequency. This definition was made by Maragos et al. under the assumptions of: (1) the bandwidth of AM or FM information signals is smaller than the carrier frequency; (2) noise free signals; (3) AM modulation is less than 100%, and FM modulation is less than 1 ($\omega_m/\omega_c<1$, where $\omega_m$ is the modulating frequency and $\omega_c$ is the carrier frequency). Therefore, implicit assumptions, when using this feature, are that the brain signals can be modeled as a summation of sinusoids with different amplitude and frequency modulation, where the bandwidth of each AM or FM part is smaller than the corresponding carrier. A possible physiological interpretation is to consider each brain signal as the sum of several nonlinear time-varying oscillators within the terminal contact area of the electrode. As is known, neuron signals are FM modulated; therefore, the many thousands of neuron voltages recorded can be divided into groups representing each oscillator. Neuron signals with the same carrier frequency and FM message will belong to the same group (same oscillator); and hence, will add up their tuned signals to produce the oscillator output. Thus, obviously, each of the oscillators would represent the response produced by thousands of neurons oscillating at the same frequency and transmitting the same FM information. There will be as many oscillators as there are different carrier frequencies and FM messages present. The AM component is determined by the number of neurons contributing to each oscillator. The more neurons that are tuned to the same frequency, the larger is the amplitude of the oscillator, creating the effect of an AM modulation. This hypothesis of multiple neuron responses adding up to each oscillator output seems reasonable considering that the NE operator makes no assumptions regarding the source of the AM and FM signals.

The NE operator is computed according to the expression:

$$NE[n]=x^2[n]-x[n-1]x[n+1].$$

The NE operator as well as the features derived from it, are instantaneous features in the sense that they provide one value for each value of the original data. Therefore, the values of the nonlinear energy feature are subject to a second level of extraction where they are weighted with a rectangular window or any other window shape; their mean value is then calculated and called average nonlinear energy. The length of this window is optimized for the data set of each patient according to the procedure described in FIG. 18 and illustrated for one of the features in FIG. 19. The average nonlinear energy is obtained as follows, $$ANE[k] = \frac{1}{N} \sum_{n=1+(k-1)(N-D)}^{k(N-D)+D} NE[n]$$

where:

ANE[k] is the average nonlinear energy at time k,

N is the window length optimized for the data of each particular patient,

D is the overlap in number of points, k is a discrete time index equal to 1, 2, 3, . . . .

It is observed that instead of using a rectangular window, by utilizing an exponential window, the results can be enhanced. This occurs because the feature values nearer to the seizure onset (more recent ones) are emphasized more than the values that occurred earlier. The exponentially weighted average nonlinear energy (WANE) is found by:

$$WANE[k] = \frac{1}{N} \sum_{n=1+(k-1)(N-D)}^{k(N-D)+D} NE[n]w[n],$$

$$w[n] = \frac{f_s}{N} e^{-n/(2f_s)},$$

where:

w[n] is the exponential window used, $f_s$ is the sampling frequency of the data signal (typically 200 Hz).

FIG. 20 shows the WANE signal for a pre-seizure and baseline record from the same patient. In this figure two bursts of enery can be observed around 25 and 5 minutes before the UEO in the preictal segment not present in the baseline segment. This feature yielded similar results across the patients studied.

Thresholded Nonlinear Energy (TNE)

From the above expression for average nonlinear energy, the thresholded nonlinear energy (a binary sequence) is derived as follows:

$$TNE[n]=\theta(NE[n]>th_1),$$

where $th_1$ is a threshold that is adjusted depending on the patient as indicated in the following expression, and $\theta$ is the Heaviside function also known as the step function.

$$th1 = \frac{C}{N_B N_k} \sum_{k=1}^{N_B} \sum_{i=1}^{N_k} x_k(i),$$

where $N_B$ is the number of records, $N_k$ is the number of points in each record, $x_k(i)$ is the ith value of the NE feature on record k, and C is a constant empirically selected to be 1.5 after an ad-hoc estimation. This constant can be adjusted on a patient basis.

Duration of Thresholded Nonlinear Energy

Figure 21:
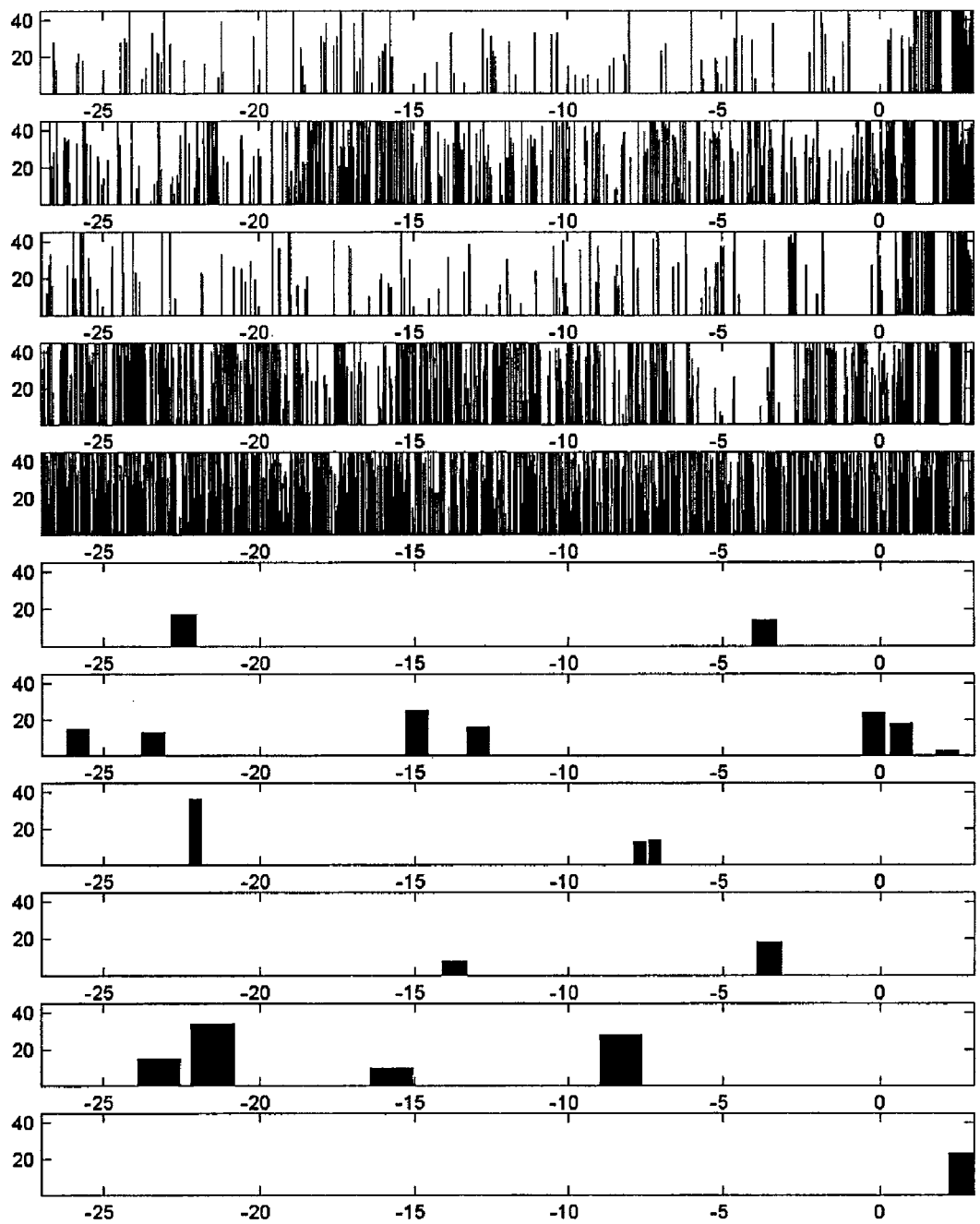
FIG. 21 illustrates the thresholded nonlinear energy in five preictal/ictal one-hour segments and six one-hour baseline segments.

The duration in an "on" state of the time series TNE(n) is determined by counting the number of consecutive ones, and creating a new sequence or feature, whose values are zero except at the end of stream of ones in the TNE(n) sequence, where this new sequence takes a value equal to the number of consecutive ones found in that stream of the TNE(n) sequence. FIG. 21 illustrates how this feature can provide encouraging results from its behavior in eleven one-hour segments that indicate a clear distinguishability between preictal and no preictal portions of data up to 50 minutes prior to the UEO. Further analysis is required to determine how long in advance this difference becomes clear.

Ratio of Short and Long Term Power or Any Other Feature

Figure 22:
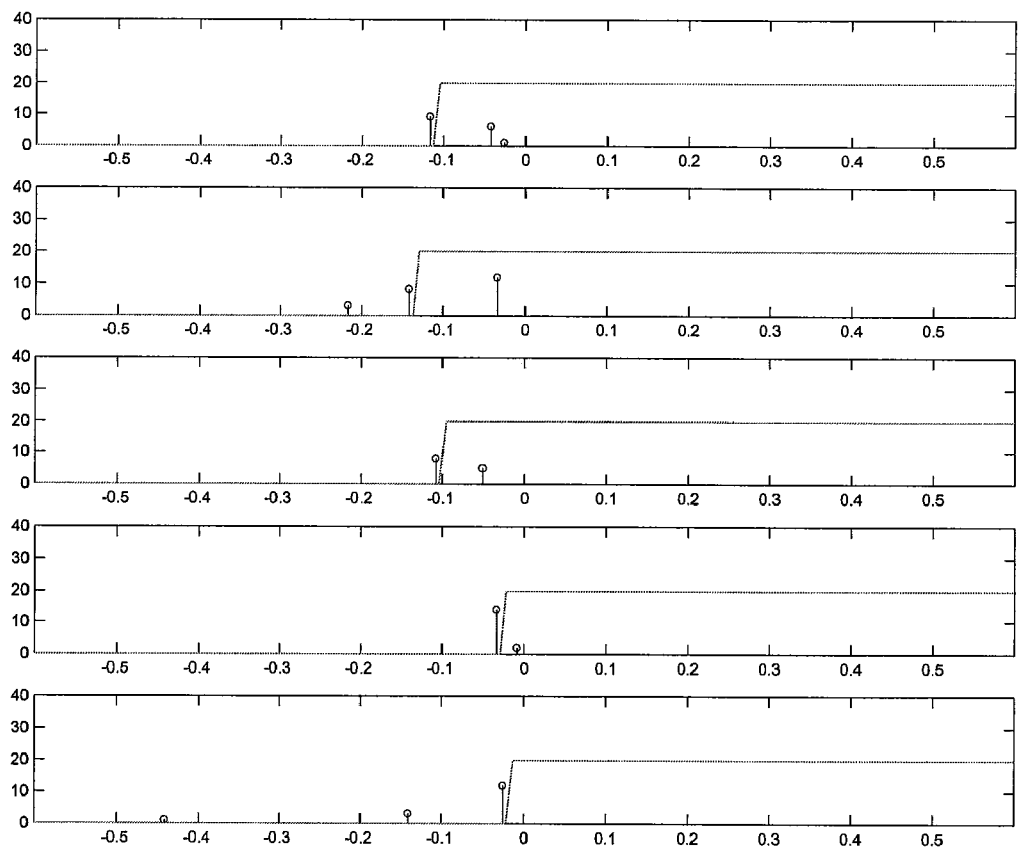
FIG. 22 illustrates the location and magnitude of the short term energy of the wavelet coefficient above the long term energy adaptive threshold.

This feature corresponds to a second level of feature extraction where once the average power is obtained, two more moving averages of the power are calculated over time for different sliding window sizes. In one case the window length is long and in the other it is short corresponding to the long term power and short term power, respectively. The ratio of these two is taken and assigned to the current time the feature is being computed. A variation of this feature includes determining when the short term power goes above or below an adaptive threshold obtained from the long term power. The same ratio or threshold crossing between a short and a long term feature can be computed for any other feature from any of the domains mentioned in this invention. The duration and magnitude by which the short term feature exceeds the adaptive threshold can also be quantified in a third level of extraction. FIG. 22 shows the times as well as the magnitude by which the short term energy of the $4^{th}$ wavelet coefficient exceeded the 20% value of the long term energy of the same coefficient. These results were computed over five one-hour preictal IEEG segments from one epileptic patient. The continuous line indicates how a continuous adaptive threshold classifier based on a duration and magnitude of the difference between the short and long term energy can provide a prediction for a time horizon around two minutes utilizing only this feature. It is expected that when more features are added into the analysis, the performance will improve. Twelve one-hour baselines where also analyzed yielding a total of 8 FPs under this raw classification scheme, which was used only for evaluation purposes.

Fractal Dimension of Analog Signals

The fractal dimension (FD) of a waveform can be computed over time by using Katz's algorithm, with very good results for early detection of the UEO. The FD of a curve can be defined as:

$$D = \frac{\log_{10}(L)}{\log_{10}(d)}$$

where L is the total length of the curve or sum of distances between successive points, and d is the diameter estimated as the distance between the first point of the sequence and the point of the sequence that provides the farthest distance. Mathematically speaking, d can be expressed as:

$$d = \max(x(1), x(r)).$$

Considering the distance between each point of the sequence and the first, point r is the one that maximizes the distance with respect to the first point.

The FD compares the actual number of units that compose a curve with the minimum number of units required to reproduce a pattern of the same spatial extent. FDs computed in this fashion depend upon the measurement units used. If the units are different, then so are the FDs. Katz's approach solves this problem by creating a general unit or yardstick: the average step or average distance between successive points, $\bar{a}$. Normalizing distances in the equation for D by this average results in, $$D = \frac{\log_{10}(L/\bar{a})}{\log_{10}(d/\bar{a})}$$

Defining n as the number of steps in the curve, then $n = L/\bar{a}$, and the previous equation can be written as:

$$D = \frac{\log_{10}(n)}{\log_{10}\left(\frac{d}{L}\right) + \log_{10}(n)}.$$

The previous expression summarizes Katz's approach to calculate the FD of a waveform. A great deal of repeatability has been observed with this feature and with the FD of binary signals across records from the same patient and even across patients ("Fractal Dimension characterizes seizure onset in epileptic patients", 1999 IEEE International Conference on Acoustics, Speech, and Signal Processing, by Esteller et al.).

Fractal Dimension of Binary Signals

The FD of digital or binay signals is calculated using Petrosian's algorithm. It uses a quick estimate of the FD. Since waveforms are analog signals, a binary signal is derived from the analog input signal by obtaining the differences between consecutive waveform values and giving them the value of one or zero depending on whether or not their difference exceeds a standard deviation magnitude or another fixed or adjustable threshold. The FD of the previous binary sequence is then computed as:

$$D = \frac{\log_{10} n}{\log_{10} n + \log_{10}\left(\frac{n}{n + 0.4 N_\Delta}\right)}$$

where n is the length of the sequence (number of points), and $N_\Delta$ is the number of sign changes (number of dissimilar pairs) in the binary sequence generated.

Curve Length

Inspired by Katz's definition of FD, the curve length is a feature that resembles the FD but runs faster because it is easier to implement in real time. It is computed as follows:

$$CL(n) = \sum_{k=n}^{n+N} \text{abs}[x(k-1) - x(k)]$$

where CL(n) is the running curve length of time series x(k), N is the sliding observation window, and n is the discrete time index. This feature plays an important role for early detection of seizure onsets.

Frequency Domain Features

This category includes all features that contain some information regarding the frequency domain, such as frequency content of the signal, frequency content in a particular frequency band, coherence, ratio of the frequency energy in one band with respect to another, crossings of the mean value in the power spectrum or in the time series, etc.

Power Spectrum

The spectrum is estimated using Welch's average periodogram, which is the most widely used periodogram estimation approach. Welch's average periodogram is given by, $$\hat{P}_W(f) = \frac{1}{P} \sum_{p=0}^{P-1} \check{P}_{xx}^{(p)}(f),$$

$$\text{where: } \check{P}_{xx}^{(p)}(f) = \frac{1}{UDT} |X^{(p)}(f)|^2, \ U = T \sum_{n=0}^{D-1} w^2[n],$$

$$X^{(p)}(f) = T \sum_{n=0}^{D-1} x^{(p)}[n] \exp(-j 2\pi f n T), \ x^{(p)}[n] = w[n] x[n + pS],$$

P is the number of sub-segments analyzed inside each input segment,

0<p<P−1 is the index range of segments, f is the frequency,

D is the length of the periodogram window, w[n] is the Hamming window, $x^{(p)}[n]$ is the weighted pth sub-segment, x[n] is the data segment, T is the sampling period, S is the number of samples shifted as the window moves through the input segment.

The power spectrum is computed using the running observation window to visualize the spectrum changes over time. Even though this feature is evaluated to characterize the bandwidth of the IEEG signals and to compare it during ictal, preictal and interictal epochs, it is really used to derive the power on different frequency bands as described below.

Power on Frequency Bands

Figure 23:
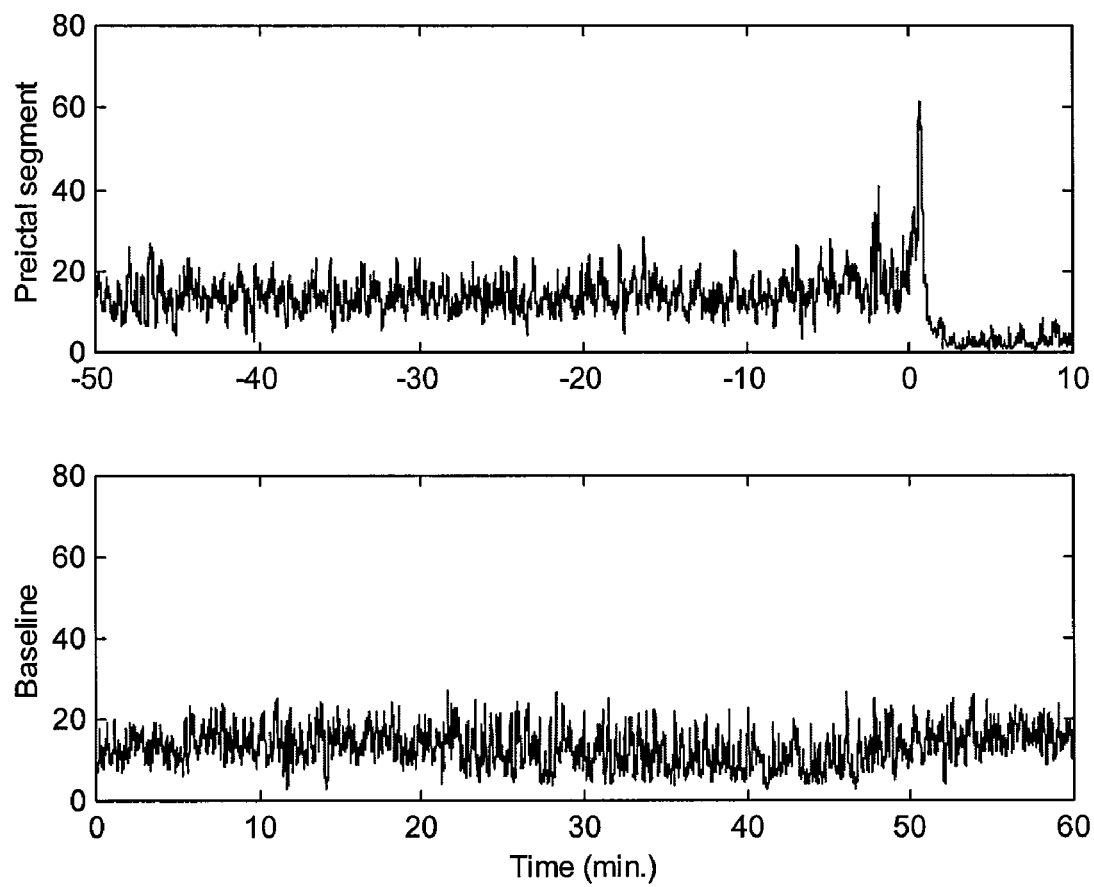
FIG. 23 illustrates the power in alpha band for preictal and baseline records.

Once the power spectrum is estimated, the power on four frequency bands can be analyzed: delta band (lower than 4 Hz), theta band (between 4 and 8 Hz), alpha band (between 8 Hz and 13 Hz) and beta band (between 13 Hz and 30 Hz). The power on each band is computed as the area under the spectrum for the corresponding frequency band (i.e., the integral of each band). The following equation represents the computation:

$$P_i = \frac{1}{P_T} \sum_{k=f_1}^{f_2} X(k),$$

where Pi is the power on the frequency band i, i can be either: delta, theta, alpha or beta band, $f_1$ and $f_2$ are the low and high frequency indices of the band under consideration, k is the discrete frequency index, X(k) is the power spectrum, and $P_T$ is the total power (integral of X(k)). FIG. 23 illustrates the power on the frequency band between 8 and 13 Hz (alpha) for a 50-minute preictal segment and a baseline segment. There is a clear difference in the power in this frequency band that between the two segments is also observed in the other segments analyzed. Around three minutes before the UEO a peak value is reached in the power of this frequency band (see FIG. 23).

Coherence

This is the signal processing name for the cross-correlation between two frequency spectra. It is calculated to explore the issue raised by some researchers, regarding a frequency entrainment or neural synchronization between the focal area and other cortical sites prior to seizure onset. Channels from the focal region and other cortical sites of the brain have been reported to exhibit some alignment in their phases for different features as the seizure approaches. The coherence between the focal channel and its homologous contralateral site is a good method for analyzing neural synchronization. It is computed using a practical method to determine the coherence between two signals, as indicated by $$C_{xy}(k) = \prod_k \frac{P_{xx}(k)}{\max_i\{P_{xx}(i)\}} \frac{P_{yy}(k)}{\max_i\{P_{yy}(i)\}},$$

where Pxx is the power spectral density of x[n], and Pyy is the power spectral density of y[n]. Note that $C_{xy}$ is the vector given by the product of each frequency value of the maximum normalized power spectral density of x, $$\max_i\{P_{xx}(i)\},$$

and the maximum normalized power spectral density of y, $$\max_i\{P_{yy}(i)\}.$$

Mean Crossings

This feature counts the number of times the signal crosses the mean value of the window segment under analysis. As the running window slides over the data, the number of crossings is calculated for each window.

Zero Crossings

The number of times the input signal crosses the zero value is counted within a pre-defined sliding observation window.

Wavelet Domain Features

Intuitively, wavelet analysis can be considered as a variable-length windowing technique. In contrast with the short-time Fourier transform, wavelet analysis can study phenomena that is localized in time. This possibility of associating a particular event characterized by a frequency component, a disturbance, etc., to a time span, is one of the major advantages of wavelet analysis. Wavelets are waveforms of limited duration with zero average value and a tendency to be asymmetric. In contrast, sine waves have smooth and symmetrical shape and infinite duration. The short-time Fourier analysis uses a time-frequency region rather than the time-scale region used by wavelet analysis. While the Fourier approach uses a fixed window length that determines the resolution, in the wavelet analysis different window lengths are used (i.e, different scales), such that if the interest is in low frequencies, long time windows are appropriate and the opposite holds true for high frequencies. Another important concept that differentiates both types of analysis is that the Fourier transform breaks the data signal into sine waves with different frequencies, and the wavelet transform breaks the data signal into shifted and scaled versions of the mother wavelet used.

Spike Detector

Figure 24:
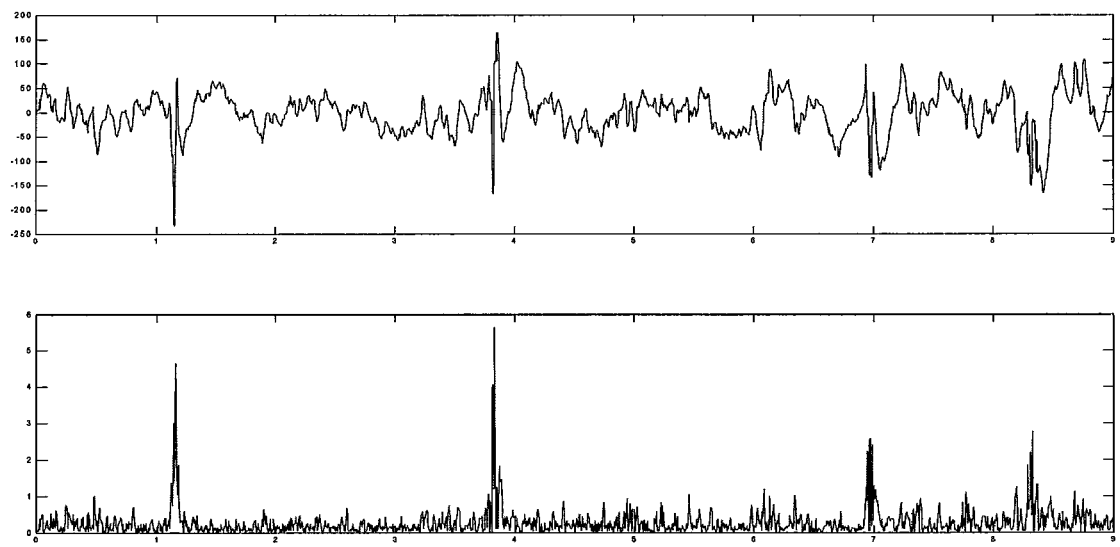
FIG. 24 illustrates an IEEG segment (top) and the spike detector output (bottom).
Figure 25:
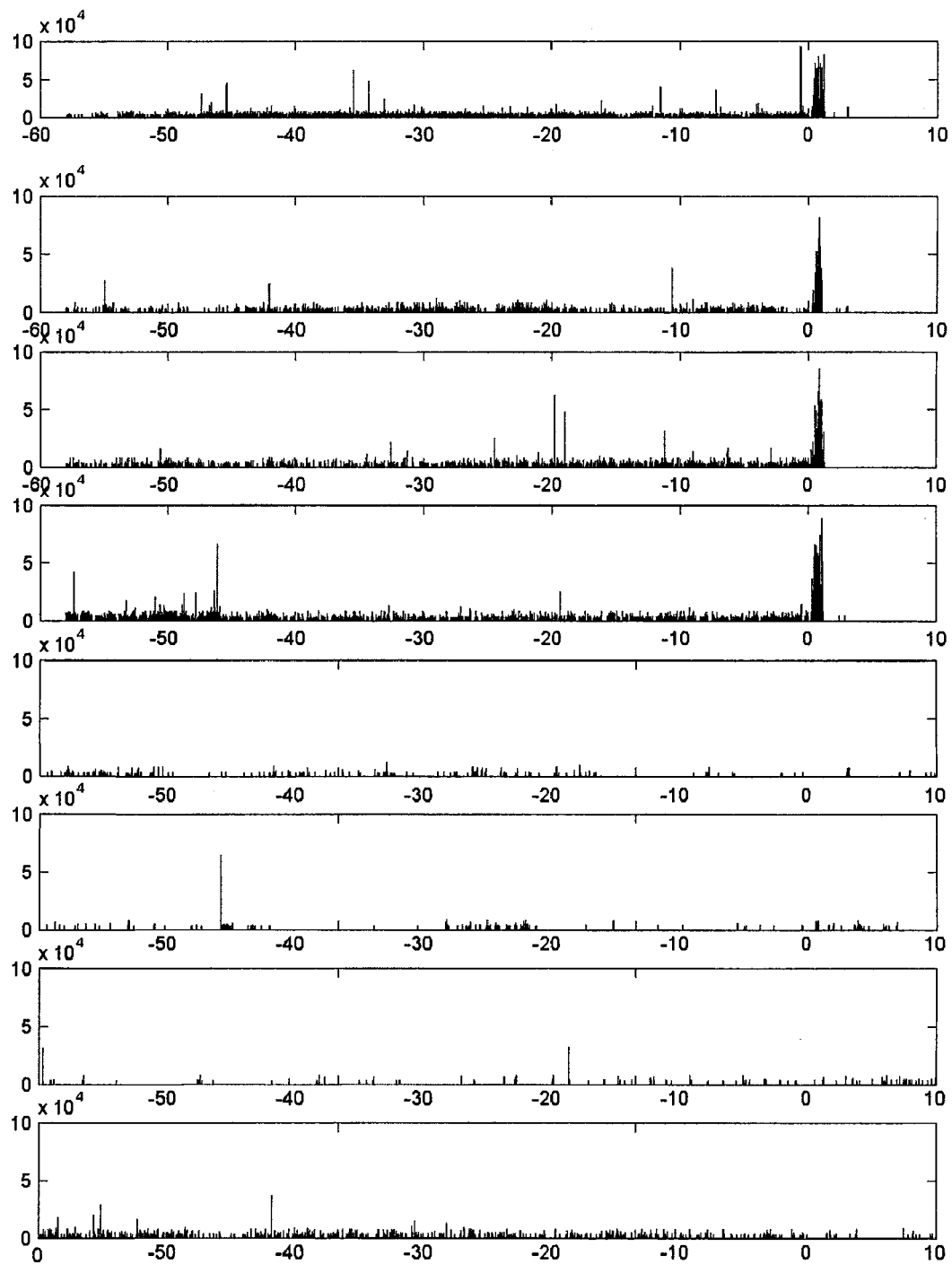
FIG. 25 illustrates the excess of the spike detector output over a pre-established threshold over time in four preictal/ictal and four baseline records.

There has been much discussion in the technical literature regarding the possibility of a relationship between the presence of spikes on the EEG signal and the occurrence of a seizure. Aimed toward testing this hypothesis, a spike detector has been developed. Initially, the NE operator was computed, but only high amplitude spikes were detected, while low amplitude spikes were missed. The spike detector developed in this invention utilizes a "prototype spike" as the mother wavelet. A set of spikes is randomly chosen from the patient, and by aligning and averaging these spikes, a "prototype spike" is created and denoted as the mother wavelet. This prototype spike is patient-tuned. Using the running window method the inner product of this "prototype spike" and the data is computed; once it reaches a value higher than a pre-established threshold a spike is detected. FIG. 24 illustrates the behavior of the spike detector for a segment of IEEG. From this figure, the spike detection is clear disregarding the spike amplitude. FIG. 25 shows the spikes detected over time in eight one-hour records for four preictal and four baselines. Each vertical line denotes a spike detected, the amplitude of the vertical line increases in proportion to the excess of the inner product over the threshold. From this figure, it is clear how a second level of extraction computing the density of spikes over another running window can distinguish between the preictal and baseline records tens of minutes prior to the seizure.

Density of Spikes over Time

Using the spike detector developed, in a second level of extraction, a threshold is used to count the number of spikes that fall in the running window over time. Results presented in FIG. 25 are encouraging to process the prediction of UEO with features of this nature.

Absolute Value of the 4th Wavelet Coefficient

Figure 26:
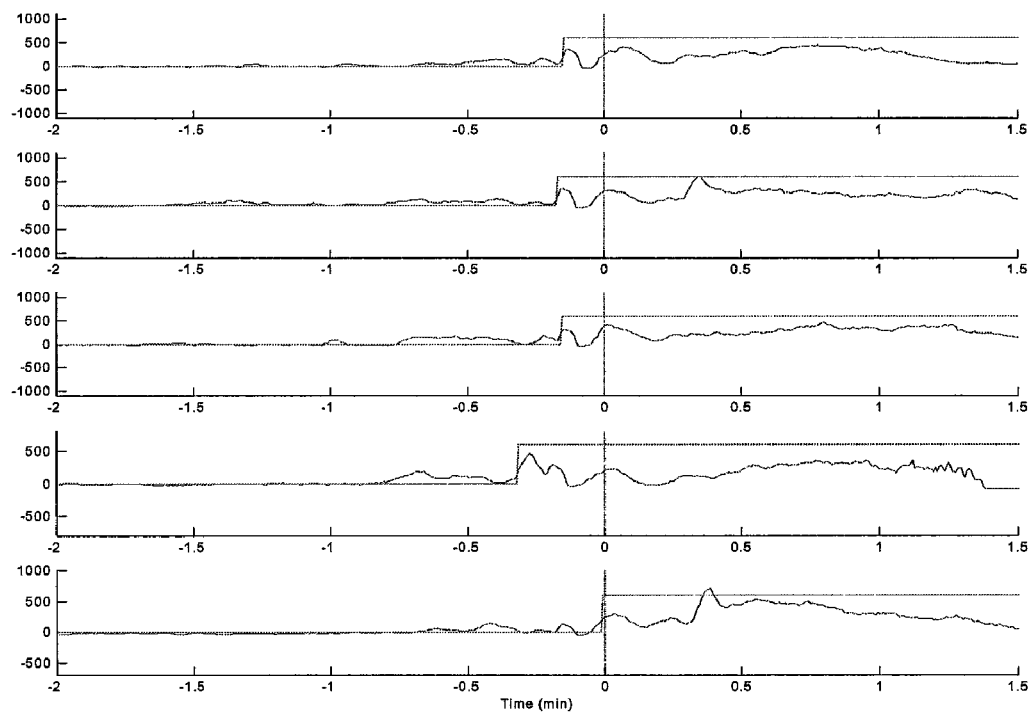
FIG. 26 illustrates the absolute value of the 4th scale wavelet coefficients average, for five seizure records from the same patient.

Results with several wavelets have been examined by visual inspection. Among the mother wavelet results observed, the one that provided the best visual separation between classes is the result obtained with Daubechies 4. The wavelet transform is run over the data for four or more different scales. The scale that provides the best distinguishability between the preictal and the ictal class is selected. FIG. 26 presents 3.5-minute epochs of five seizures from the same patient, extracted for the one-hour preictal records analyzed. A clear elevation starts between one minute and a half-minute before the seizure UEO. Using a basic threshold classifier a typical prediction time based on only this feature would be around two minutes. Twelve one-hour baseline segments were also analyzed using this feature in this patient with the same simple threshold classifier, yielding only one FP. This seems to be a good feature to use as part of the feature library. Similar results were found across patients. This feature was initially analyzed for 6-minute records instead of 1-hour records, because it generates one feature value for each IEEG sample, therefore, it has no data compression. However, after the second level of extraction is conducted, where a running window is slid over the wavelet coefficients and the mean of their absolute value is calculated for the feature values within each window, it resulted in data compression, while preserving most of the feature information and decreasing variability. The window length varied from patient to patient, depending on the result of the window size optimization described below.

Statistics and Stochastic Processes

From the huge variety of features in the statistical domain, the mean frequency index, the cross-correlation, and the coeffients of an autoregressive (AR) model are among the ones included in the feature library of the present invention.

Mean Frequency Index

This is a measure of the centroid frequency, calculated as follows:

$$mf = \frac{fs}{N} \frac{\sum_{i=1}^{N/2}(i-1)x_i}{\sum_{i=1}^{N/2} x_i},$$

where fs is the sampling frequency, N is the length of the IEEG segment, and $x_i$ is the magnitude of the power spectrum.

Figure 27:
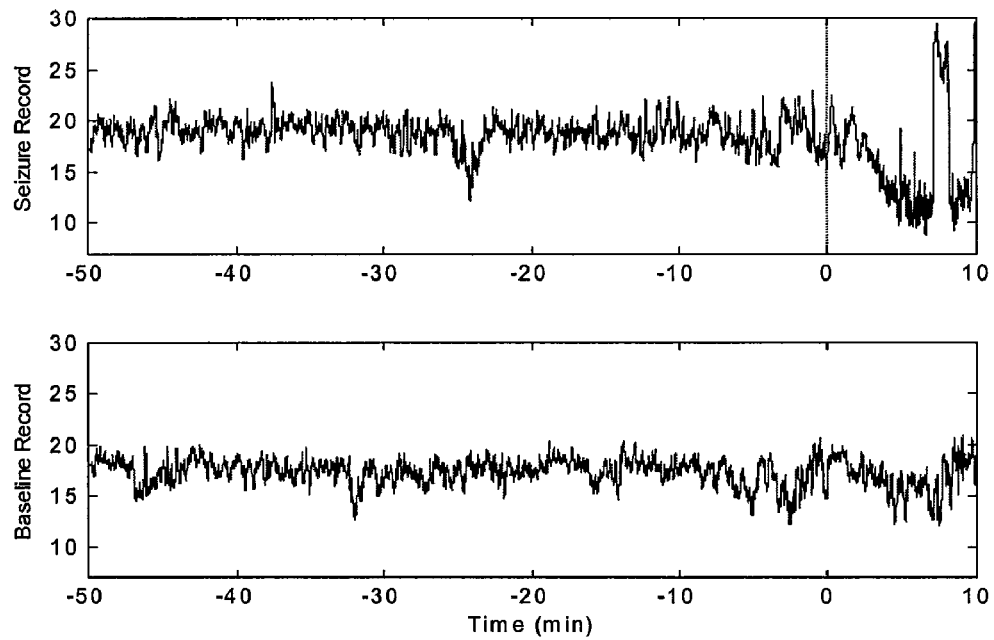
FIG. 27 illustrates graphs of the mean frequency of a seizure (top) and a baseline (bottom).

FIG. 27 shows the mean frequency index of a seizure and a baseline record over time for a window length of 2000 points or equivalently 10 seconds. The vertical line at time zero emphasizes the UEO time. It is clear from this figure, that the mean frequency can be a useful feature for seizure UEO prediction/detection considering the small elevation of the average frequency as the seizure approaches which is not observed during baseline periods away from ictal activity. Note the presence of sudden periodic peaks above 20 Hz starting around 12 minutes before the seizure UEO. Other records in the database exhibited a similar behavior. This feature may be enhanced to increase the distinguishability between preictal and no-preictal records, by either utilizing a different shifting and window length, or by an additional processing at a third level of extraction, such as averaging, detection of the maximum value over a third running window, ratio of short term versus long term frequency index, etc. The clear issue is that the mean frequency index may provide a smoother feature with less variability over time and better results.

Cross-Correlation

The consideration of this feature is motivated for the same reasons that encouraged the coherence analysis between homologous contralateral channels. The cross-correlation can reflect the degree of similarity between different channels, therefore, if a synchronization takes place, at some point before the seizure, this feature should be able to sense a change in that direction. The mathematical expression to compute the cross-correlation is given by $$R_{xy}(m) = \frac{1}{N} \sum_{n=0}^{N-m-1} x[n+m]y*[n], \text{ for } 0 \le m \le N-1.$$

Figure 18:
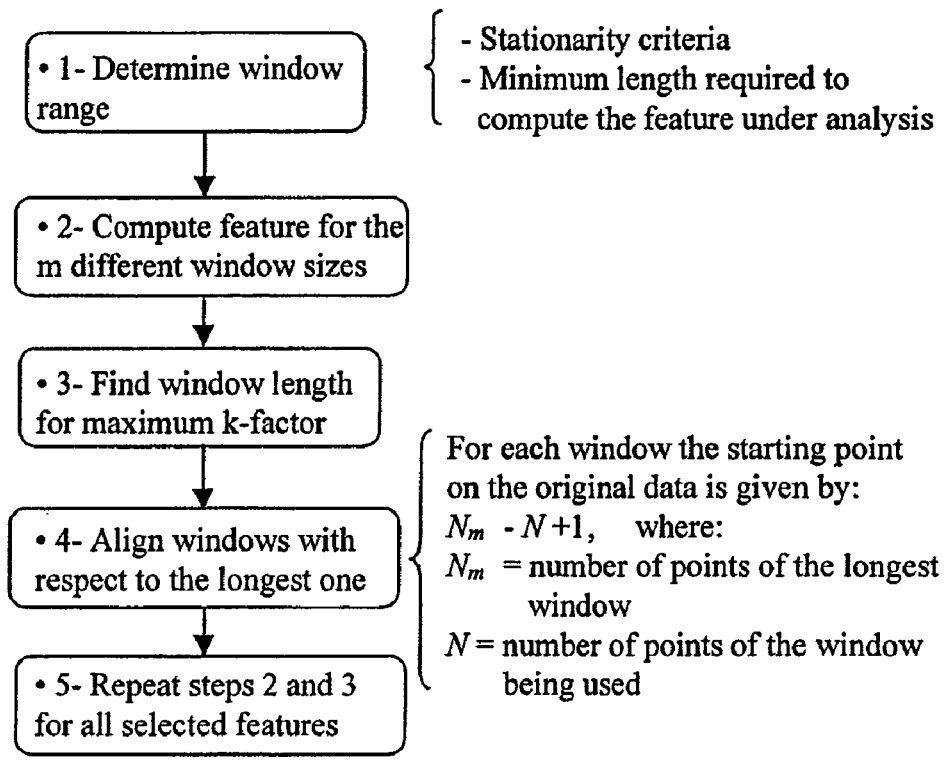
FIG. 18 illustrates the processing logic for the selection of the sliding observation window size for maximum distinguishability between classes.
Figure 19:
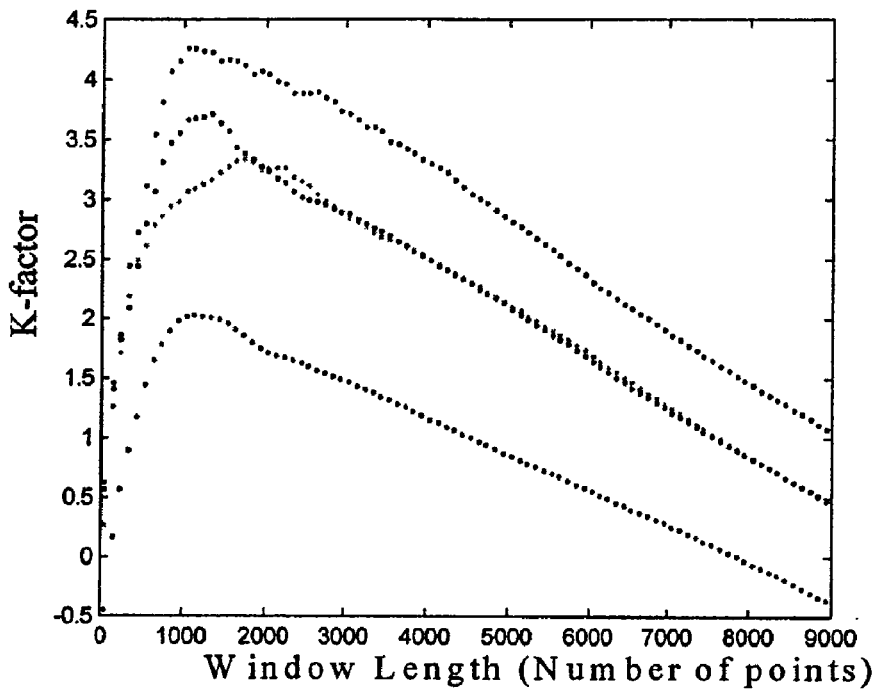
FIG. 19 illustrates the k-factor as a function of the window length for the weighted fractal dimension in four different records.

The running cross-correlation is computed for each sliding observation window used according to the window selection procedure summarized in the flowchart of FIG. 18 and exemplified in FIG. 19. Each time the cross-correlation is calculated, a sequence of values is obtained for the different lags, the maximum cross-correlation value from all the different lags is the one kept over time for the generation of this feature.

Autoregressive (AR) Coefficients or Linear Prediction Coefficients

A time series model often used to approximate discrete-time processes is the AR model whose time domain difference equation is:

$$x[n] = -\sum_{k=1}^{p} a[k]x[n-k] + u[n],$$

where p represents the AR model order. From this expression, it is clear that the sample at time n is being estimated from the p previous samples and the present input. In time series analysis where no input is available, u[n] is considered as white gaussian noise error between the real present sample x[n] and the sample estimated without input. A forward linear predictor is used to estimate the AR coefficients. Defining the error variance as $$\rho = E\{|e^f[n]|^2\},$$

where $$e^f[n] = x[n] - \hat{x}^f[n],$$

then, the forward linear prediction estimate is $$\hat{x}^f[n] = -\sum_{k=1}^{p} a^f[k]x[n-k].$$

Computing the error variance from the error definition above, and substituting the forward linear prediction estimate yields the following equation $$\rho = r_{xx}[0] + \underline{r}_p^H \underline{a}^f + (\underline{a}^f)^H \underline{r}_p + (\underline{a}^f)^H R_{p-1} \underline{a}^f,$$

where:

$\underline{a}^f$ is a vector with the AR coefficients, $\underline{r}_p$ is a vector with the autocorrelation for lags 1 to p, and $R_{p-1}$ is the autocorrelation matrix, H represents the conjugate transposed.

The AR coefficients can be found by minimizing the last equation. Preliminary results suggest this feature has potential for prediction.

Information Theory Features

Features from the information theory domain are available in the feature library, including the entropy as originally defined by Shannon, and the mutual information function. It has been hypothesized that the level of organization changes before, during and after a seizure; thus, these features must be analyzed to explore this possibility.

Entropy

Entropy is a measure of "uncertainty," and is heavily used in the information theory field. The more uncertainty there is regarding the outcome of an event, the higher is the entropy. The entropy is computed by using:

$$H = -\sum_{i=1}^{20} pdf(i)\log_2(pdf(i)),$$

where pdf in this setting stands for the probability distribution function. It is found by dividing x (i.e., IEEG data segment) into 20 different amplitude containers, determining how many values of x are in each container, and normalizing by the number of values in the observation window. Thus, the pdf is a 20-bin histogram normalized to represent discrete probabilities. Note that i in the above expression indicates the container number. A different number of containers can be chosen depending on the length of the sliding observation window used.

Average Mutual Information

This feature is explored with the idea of finding a relation between the information in the focal channel and the homologous contralateral channel. This feature is also considered as a nonlinear cross-correlation function. The mathematical expression used for the computation of the average mutual information is:

$$I_{AB} = \sum_{a_i,b_j} P_{AB}(a_i, b_j)\log_2\left[\frac{P_{AB}(a_i, b_j)}{P_A(a_i)P_B(b_j)}\right],$$

where:
$P_{AB}$ is the joint probability distribution of A and B,
$P_A$ is the probability distribution of A, and
$P_B$ is the probability distribution of B.

Window Length Selection

Several factors are taken into account when determining the window length to be used in the analysis. Among them are data stationarity, data length required to compute the features, sampling frequency, maximizing the distinguishability between preictal and ictal segments, and maximizing the accuracy in the prediction time. A compromise has to be achieved between the requirement of a window sufficiently long to compute specific features and a window short enough to assume data stationarity. An IEEG segment of tens of seconds can be considered quasi-stationary, depending on the patient's behavioral state. This depends also on the type of input signal under consideration, for example chemical concentrations may be considered quasi-stationary over a longer time frames.

An original methodology for selecting the window size is introduced here. This methodology arises as an answer to the issues of how to effectively select the window size to compute specific features and how to create the feature vector when the features extracted have different lengths. These questions emerged during the development of the feature extraction stage of this invention. The goal of this technique is to maximize the distinguishability between the preictal/ictal class and baseline class. The processing logic of FIG. 18 and results of FIG. 19 summarize the procedure. In this scheme, each of the features pre-selected is computed for different sliding window sizes. The k-factor is used as the performance criteria that guides the window size selection by quantifying class-separability and variance, however any other performance measure suitable for this purpose can be used.

Ninety different window sizes or less are selected within the range of 50 points (0.25 seconds) to 9000 points (45 seconds). This window range is selected to include the maximum window size to satisfy quasi-stationarity of the data segments and the minimum window size required to compute the feature. All these windows are shifted according to either of the following two criteria. The windows are shifted by a fixed shift of 90 points (0.45 seconds) along the input sequence, or by the shift that corresponds to preserving a 50% overlap in the running window methodology. The running window method described earlier is used to generate the features. These 90-point shifts or 50% of window length shifts fix the minimum prediction time to 0.45 seconds or to the time shift that corresponds to the 50% of the window size used. The maximum delay in the UEO detection is also the same as the time shift, assuming optimal features, as those capable of detecting the seizure onset as soon as one sample of the ictal input data is within the sliding window. There is also a trade-off between this window shifting or time resolution and the storage capacity of the system. The shorter this time resolution or the smaller the window shifting, the greater the memory space required.

After each feature is computed for the different windows, the k-factor in the following equation is computed as a measure of effectiveness of each feature.

$$K = \frac{|\mu_1 - \mu_2|}{\sqrt{(\sigma_1^2 + \sigma_2^2)/2}},$$

where:
K is the k-factor (measure of effectiveness of the feature),
$\mu_i$ is the mean of feature for class i,
$\sigma_i^2$ is the variance of feature for class i.

Around 20% of the available preseizure records are used to determine the best window length to use. For each pre-seizure record used, the window size corresponding to the maximum k-factor is chosen to precede the analysis. Then, a verification follows to confirm that the window lengths that maximize the k-factor in each record are clustered around some value. The center of the cluster of "optimal" window lengths is chosen as the window length for the feature under consideration. FIG. 19 illustrates the variation of the k-factor for the fractal dimension feature, as the window size is changed for four different seizure records. The so-called "optimal" window length is within approximately 1000 and 1500 points in this case.

Typically, the window sizes that maximize the k-factor are different for each feature. Therefore, a strategy is required to allow the creation of feature vectors from features extracted with different sliding window sizes and sometimes also with different window shiftings, which implies that the features do not coincide in time and have different time spans between consecutive values. One way to obtain a perfect time alignment and identical time span across features, is by satisfying the following two conditions. The first condition guarantees the same time span for consecutive values on all the features. This is achieved by making the observation window displacement equal for all the window sizes on all the features. The second condition requires the alignment of all the observation windows with respect to the right border of the longest window, as shown in FIG. 28. The effect of applying equal displacement of the observation window even for features with different window sizes is that the number of overlapping points on each observation window will change from feature to feature, while the shifting points will remain constant. Therefore, as a way to preserve the percentage of overlap for all the features or to even have different percentages of overlap and different shiftings (making the system more general), a second alternative can be followed. It is to align the features in time by resampling them. In this form, the features with less samples can be upsampled by adding as many values as needed. For example, if the upsampling is by three, then each value of the feature sequence will be repeated twice.

Using any of the two approaches described, historical and instantaneous features can be combined by extracting historical features from the instantaneous features utilizing a shift of one-feature-sample for the observation window, upsampling if necessary to achieve a correct time alignment of the historical features and the instantaneous ones. Intuitively, this type of approach can outperform those that rely only on instantaneous features. An example is the use of delta features in speech processing.

When the feature-parameter approach is used, the feature selection is a required procedure performed by the supervisory control 400 that involves the extraction of features within the feature library and the analysis to select the "optimal" set of features.

Feature selection deals with determining the smallest subset of features that satisfies a performance criterion once the set of candidate features has been extracted. Candidate features must be ranked by their effectiveness to achieve class separability. This implies that feature selection is also a feature optimization problem, where an optimal feature subset has to be chosen from the combinatorial problem of finding a subset with the best M features out of N original features. Several issues must be considered for the feature selection, such as minimization of numerical ill-conditioning, maximization of discrimination among classes, maximization of orthogonality, selection of classifier topology, and computational loading for real-time implementation.

Typical causes of ill-conditioning are large differences in the orders of magnitude between pairs of features, statistical correlation between any pair of features, a large number of features, and a small number of training feature vectors. To reduce ill-conditioning problems, features must be normalized so that different scaled feature values will have the similar mean and variance. A basic normalization scheme can be achieved by using the expression:

$$\check{f}_k(n) = \frac{f_k(n) - \mu_k}{\sigma_k},$$

where:
$f_k(n)$ is the nth sample from feature k,
$\check{f}_k(n)$ is the nth sample normalized from feature k,
$\mu_k$ is the average over all feature samples from all classes,
$\sigma_k$ is the standard deviation over all feature samples from all classes.

Thus, $\mu_k$ and $\sigma_k$ are computed as:

$$\mu_k = \frac{1}{N}\sum_{i=1}^{N} f_k(i) \text{ and } \sigma_k = \sqrt{\frac{1}{N-1}\sum_{i=1}^{N}(f_j(i) - \mu_k)^2}.$$

The implementation of the previous normalization scheme in an on-line fashion requires the computation of the average and standard deviation over a long term running window that covers part of the feature history. The length of the window for computing the parameters required for feature normalization depends on the probability time horizon under consideration. A typical window may be ten times or more the time horizon analyzed. There is a trade-off between this historical window and the memory available within the implantable device.

In addition, some correlation studies can be helpful to select a final group of features that synergistically contributes to the onset detection task. These can be performed by the supervisory control at the coordination level.

The feature vector optimization is performed initially in four major steps following a scheme of multi-dimensional feature optimization. This procedure can evolve into a single-dimensional feature optimization, if the correlation and complementary nature of the features involved is qualitatively acceptable implying that the final feature set obtained by both procedures (single and multi-dimensional) is about the same. The fundamental aspects of the multidimensional scheme that can also be used are summarized in the following steps:

Step 1: An initial basic pre-selection is used to discard features with evidently inferior class separability, by assessing the mean and standard deviation differences in data segments from preictal and no-preictal conditions.

Step 2: Individual feature performance is evaluated using one or more criteria for every feature that is not discarded during the initial basic pre-selection.

Step 3: Features are ranked according to their performance measure by an overlap measure criteria and then a modified version of an add-on algorithm combined with heuristics is used to select the final feature set.

Step 4: Two-dimensional feature spaces are constructed and evaluated to validate qualitatively the implicit assumption of complementarity and low correlation among the final feature set.

Considering that the performance of single dimensional feature optimization is slightly lower (typically between 3 and 8%) than its multidimensional counterpart, it provides an acceptable optimization. However, if the feature correlation is such that the features are not complementary, a multidimensional feature optimization approach is preferred. A computational assessment of the feature space is utilized to evaluate the complementarity among the features involved. The previous steps and considerations are followed by the internal program residing in the high level supervisory control 400 at the coordination layer.

A measure of overlap between the two classes involved (pre-seizure and no pre-seizure class) can be achieved on the estimated conditional probability distribution function (PDF) of the feature under analysis for each class. FIGS. 29A and 29B present two examples of curves proportional to the feature PDFs estimated directly from the data set for each class in two patients of the database. The curve with the peak in the left is proportional to the estimated PDF of the weighted fractal dimension (WFD) obtained from the actual data values of the WFD in no pre-seizure segments that include baseline records. This can be expressed mathematically as p(x|NPS), which means the PDF of feature x (in this case the WFD) given that the feature data belongs to the no pre-seizure class (NPS). The curve whose peak is in the right side of the figure, is proportional to the estimated PDF of the WFD given data from the pre-seizure class (p(x|PS)). The pre-seizure (PS) class is defined as the segments whose length is identical to the time horizon under analysis and whose ending point is right before the seizure UEO. The two graphs correspond to two different patients studied. During the analysis of the data, it was observed that the PDF depicted by the curve whose peak is in the right side of FIG. 29B, if plotted including the whole seizure time (about 3 min.) as if it were from the preictal class, then the PDF becomes multimodal. In fact, this can be inferred by looking at the trend of the left curve for low values of the WFD in FIG. 29B. This was not always the case in every patient, but it was an interesting observed behavior.

The overlap between the two classes is assessed by integrating the shaded region in FIGS. 29A and 29B, as stated according to:

$$ov = \int \min(p(x|PS), p(x|NPS)) dx,$$

where:

ov is a measure of overlap between the feature classes, p(x|NPS) is the PDF of feature x given no seizure onset class, x is a variable representing the feature for both classes, p(x|PS) is the PDF of feature x given the seizure onset class.

Note that the better the class distinguishability for a particular feature, the lower this overlap measure. The overlap measure is very general in the sense that it works under multi-modal distributions. Using the previous equation the features can be ranked individually, preparing the ground to start the multiple-dimension feature optimization.

In those problems where the class boundary is very complex and a substantial overlap is obtained in the one-dimensional feature space, a multidimensional feature optimization is the path to follow. This type of approach is computationally more intensive than single-dimension feature optimization, but it has the advantage of compensating for the correlation among features.

Figure 30:
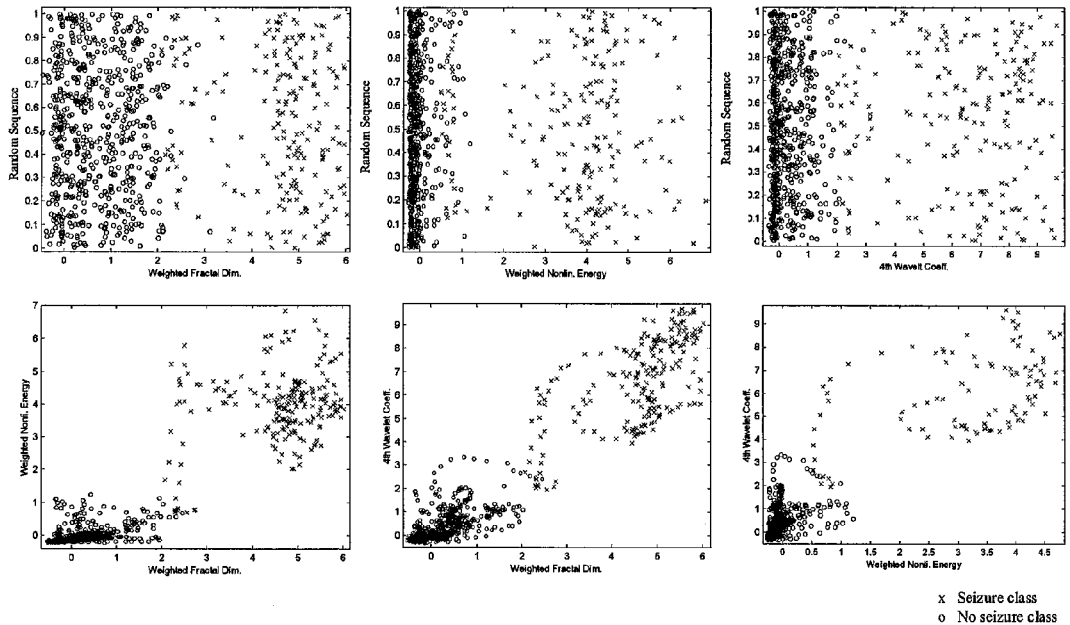
FIGS. 30 and 31 illustrate scatter plots demonstrating the complementarity of features for two different patients in 1-dimensional and 2-dimensional plots.
Figure 31:
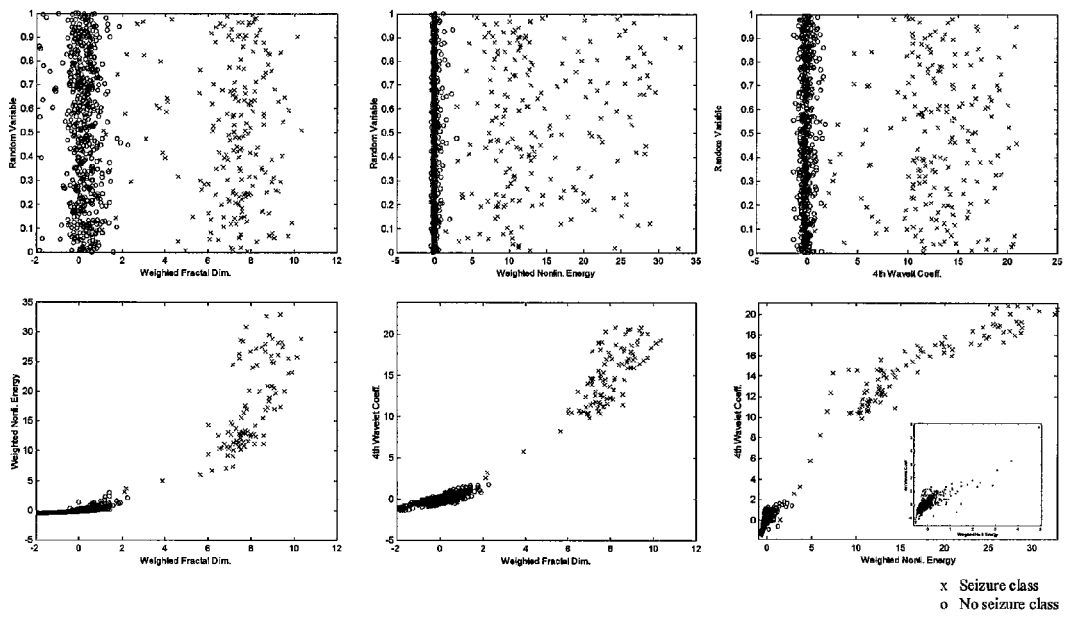

FIGS. 30 and 31 show the qualitative results from the construction of the 2-D feature space for some of the final pairs of features in the final feature set of one of the patients studied. This reinforces the idea that features are complementary. The top graphs in FIGS. 30 and 31 correspond to the 1-D feature spaces of each of the three features selected, plotted in a 2-D graph for visualization purposes. The representation of each 1-D plot as a 2-D plot is achieved by assigning a random value to correspond with each feature value. In both figures it is observed how combined features enhance the performance by decreasing the overlap between the classes.

Following the single dimensional feature optimization approach for all the patients studied, the final feature set coincided for almost all the patients when using the overlap measure and when using other performance criteria such as the Fisher discriminant ratio (FDR). The overlap criteria provides a more reliable distinguishability measure between the classes since the FDR is a linear measure based on the 1st and 2nd statistical moments while the overlap measure is based on the PDFs that implicitly contain the information of all the statistical moments. Therefore, even when the FDR measure suggested a slightly different final feature set (where at most, one of the features was different), the overlap measure is chosen as the criterion to determine the final feature selection.

Patients with Multiple Focus Regions

In patients where the seizures arise from more than one focal region, multiple electrodes are implanted in each region. The approach followed in these cases is the same as that described above, with two possible variations regarding the fusion of information. In one variation, the input signals from adjacent electrodes are subtracted forming a bipolar signal, and then bipolar signals from different focus regions are combined at the data level; in the other variation, the input signals are combined at the feature level. The second variation implies that features computed with the same algorithm and perfectly coincident or aligned in time are combined into a single feature by using a nonlinear procedure. Similarly, the first variation implies the combination of the intracranial EEG data or any other sensor data, before or after the preprocessing stage, into a single data stream. A method for the nonlinear combination of the input signals either at the data or at the feature level is to take the maximum of the two or more signals at every sample time. Besides this nonlinear combination, there are many other techniques that can be used to combine or fuse these signals or channels.

The combination of signals at the data and/or feature level can also be performed in patients with a unique focal region, where the complementarity among the signals or features from electrodes placed in different regions enhances the prediction results.

Analysis/Classification

A classifier can be viewed as a mapping operator that projects the M selected features contained in the feature vector onto a d-dimensional decision space, where d is the number of classes in the classification problem. In the classification problem under investigation for this invention, d=2 and M is chosen typically to be within the range of one to six. It is definitely true that the feature extraction and selection plays a crucial role in the classification results; however, it is highly important to select a classifier architecture suitable to the underlying feature distribution to obtain better performance recognition.

As a benchmark and proof-of-concept, a radial basis neural network (RBNN), without the usual iterative training algorithms, has been used. Particularly, a Probabilistic Neural Network (PNN) has been used within this invention for its suitability for classification problems and its straightforward design. The PNN is a nonparametric classifier, and as such it does not make assumptions regarding the statistical distribution of the data. This neural network is also called kernel discriminant analysis, or the method of Parzen windows.

Figure 32:
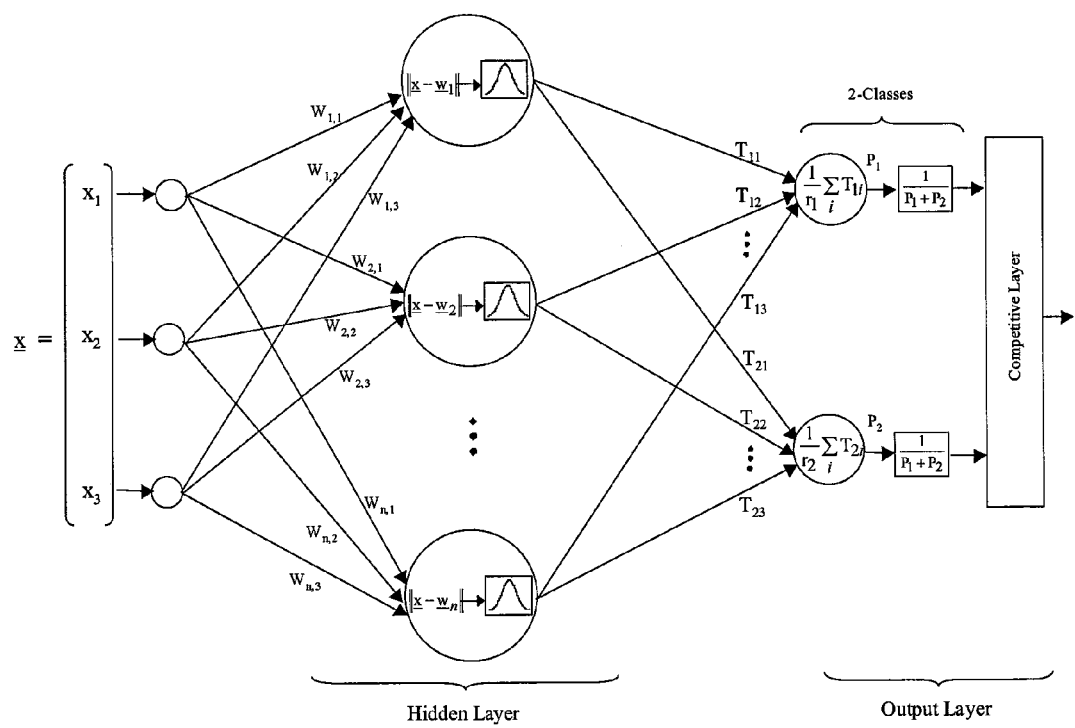
FIG. 32 illustrates an exemplary probabilistic neural network (PNN) architecture.

FIG. 32 illustrates the PNN architecture which corresponds to one of the embodiments of this invention. In other embodiments, different neural networks can be used or a combination of a neural network with a fuzzy system can be utilized. The weights used at the hidden layer of the PNN are directly the training vectors used. As can be seen in FIG. 32, this type of network requires one node for each training vector $W_k$, which represents a major disadvantage since the amount of computation involved to reach a classification, slows down its operation. Increasing the memory capacity such that the PNN can be wired (run in parallel) can decrease the computational burden and accelerate the classification. On the other hand, an advantage of the PNN is its convergence to an optimal Bayesian classifier provided it is given enough training vectors, and under equiprobable spherical class covariances for the particular implementation used in this invention.

The architecture illustrated in FIG. 32 corresponds to the particular case of a two-class problem, with three-dimensional feature vectors, $$\underline{x} = [x_1 x_2 x_3]^T.$$

Every weight $W_{kj}$ in the hidden layer is the jth component of the kth feature vector in the training set, where the kth feature vector is given by $$\underline{W_k} = [w_{1,k} w_{2,k} w_{3,k}]^T$$

where k=1, 2, ..., n and n is the number of feature vectors (patterns) in the training set. The output layer estimates the probability of having a seizure, given the input feature vector. This translates into the probability that the input signals belong to the pre-seizure/seizure class (preictal class) or to the non-pre-seizure class (baseline class), given the input feature vector, and is mathematically represented by:

$$P_1 = P(PS|\underline{x})$$

and $$P_2 = P(NPS|\underline{x})$$

where PS is the "pre-seizure/seizure class" and NPS is the "non-pre-seizure class". Matrix T contains the weights on the output layer, which indicate the corresponding class of each training feature vector, in the 1-of-k binary feature format, as typical in supervised learning approaches like this.

This architecture can be perceived in two ways. In one interpretation the Euclidean distance $z_k$ between each input feature vector $\underline{x}$ and each of the training vectors $\underline{w}_k$ is computed at each node $\|\underline{x}-\underline{w}_k\|$ in the hidden layer and passed through a Gaussian window $e^{-z_k^2/\sigma^2}$, where $\sigma^2$ is a width parameter of the window. The second interpretation is more from a neural network point of view, and considers that each input feature vector $\underline{x}$ is evaluated at n Gaussian windows with each one centered at a different training feature vector $\underline{w}_k$, k=1, ..., n, and with variance $\sigma^2$.

The present invention is realized in a combination of hardware and software. Any kind of computer system or other apparatus adapted for carrying out the methods described herein is suited. A typical combination of hardware and software could be a general purpose computer system with a computer program that, when loaded and executed, controls the computer system such that it carries out the methods described herein. The present invention can also be embedded in a computer program product which includes all the feature enabling the implementation of the methods described herein, and which, when loaded in a computer system is able to carry out these methods.

Computer program instructions or computer program in the present context means any expression in any language, code, or notation or a set of instructions intended to cause a system having an information processing capability to perform a particular function, either directly or when either or both of the following occur: (a) conversion to another language, code, or notation; (2) reproduction in a different material form.

In light of the above teachings, those skilled in the art will recognize that the disclosed methods, formulas, algorithms, and embodiments may be replaced, modified, or adapted without departing from the spirit or essential attributes of the invention. Therefore, it should be understood that within the scope of the appended claims, this invention may be practiced otherwise than as exemplified herein.

What is claimed is:

1. An adaptive multi-level hierarchical control system for predicting and controlling an electrographic onset of a seizure and other neurological disturbances in an individual, comprising:
   a data generation component, including a plurality of sensors adapted to be attached or implanted, that acquires a plurality of physiological signals detected by at least one sensor;
   an intelligent data processing device that processes the physiological signals to extract features and analyzes and classifies the extracted features to form a feedback vector that includes an estimate of a probability of seizure for at least one specific time frame;
   a low level controller including a stimulation device, having a plurality of actuators, that is activated to apply a preventive measure adaptively in response to the estimate of a probability of seizure in the feedback vector exceeding an adaptive threshold to control the onset of seizure and to adjust automatically an internal parameter setting in at least one actuator in the stimulation device; and
   a high level supervisory controller including a knowledge database and a processor that adapts to feedback vector changes over time and re-tunes the intelligent data processing device parameter settings dynamically.

2. The adaptive multi-level hierarchical control system of claim 1 wherein the knowledge database comprises a priori information for the individual.

3. The adaptive multi-level hierarchical control system of claim 2 wherein the a priori information for the individual comprises seizure frequency over time, seizure duration, type of seizure, and aura frequency collected before an implantation of the intelligent data processing device.

4. The adaptive multi-level hierarchical control system of claim 1 wherein the low level controller determines and adjusts the parameter settings of the actuators in the stimulation device continuously.

5. The adaptive multi-level hierarchical control system of claim 1 wherein the high level supervisory controller can operate in an automatic mode or in a semi-automatic mode.

6. The adaptive multi-level hierarchical control system of claim 5 further comprising a program module, cooperative with the low level controller and the high level controller, wherein the program module includes an applied feedback control law and a knowledge base control law, monitors a set of controlled variables, including the probability of seizure for at least one specific time frame, and updates the applied feedback control law when operating in the automatic mode.

7. The adaptive multi-level hierarchical control system of claim 5 further comprising a program module user interface, wherein the parameter settings are input directly into the intelligent data processing device through the program module user interface when operating in a semi-automatic mode.

8. The adaptive multi-level hierarchical control system of claim 1 wherein the high level supervisory controller comprises a processor external to the intelligent data processing device for providing a coordination layer control.

9. The adaptive multi-level hierarchical control system of claim 8 wherein the coordination layer control determines control parameters including parameters related to fusion of sensory data, feature extraction, feature normalization, neural network retraining, fuzzy logic adjustments, and fault diagnoses of the plurality of actuators, the plurality of sensors and the intelligent data processing device.

10. The adaptive multi-level hierarchical control system of claim 1 further comprising an external processor for providing a research layer control including a plurality of algorithms executable on the external processor for evaluation including algorithms for control of seizures or brain disturbances, for prediction and detection of the unequivocal electrographic onset of seizure, for control strategies, or for other types of parameter adjustments.

11. The adaptive multi-level hierarchical control system of claim 10 wherein the research layer control analyzes a plurality of data extracted from the physiological signals to evaluate seizure and other brain disturbances.

12. The adaptive multi-level hierarchical control system of claim 10 wherein the research layer control collects information from a plurality of individuals to form a research and development database.

13. The adaptive multi-level hierarchical control system of claim 6 wherein the multi-level hierarchical control is provided by the feedback control law updated by the low level controller and the knowledge base control law updated by the high level supervisory controller.

14. The adaptive multi-level hierarchical control system of claim 13 wherein the adaptive hierarchical control is provided by the updated knowledge base control law.

15. The adaptive multi-level hierarchical control system of claim 6 wherein the high level supervisory controller processor operates a logic module that executes optimization algorithms and determines self-evaluation metrics to establish the supervisory controller's performance over time, to determine required adjustments in the intelligent data processing device's set points, and to generate the updated feedback control law that is downloaded into the intelligent data processing device.

16. The adaptive multi-level hierarchical control system of claim 1 wherein the knowledge database is updated at discrete steps by downloading information from the intelligent data processing device.

17. The adaptive multi-level hierarchical control system of claim 11 further comprising an external portable module including an external communications unit that enables the transfer of the extracted physiological data from the intelligent data processing device to the external portable module for analysis and storage.

18. The adaptive multi-level hierarchical control system of claim 17 wherein the external portable module further comprises a display device that shows the probability for having a seizure in at least one specific time frame.

19. The adaptive multi-level hierarchical control system of claim 17 wherein the external portable module further comprises an alarm device, coupled to the low level controller, that is activated to alert the individual of an oncoming seizure when the probability of having a seizure in the at least one specific time frame exceeds an adaptive threshold.

20. The adaptive multi-level hierarchical control system of claim 1 wherein the intelligent data processing device is implantable.

21. The adaptive multi-level hierarchical control system of claim 20 wherein the intelligent data processing device comprises artificial intelligence tools wherein the intelligent data processing device provides a learning capability based on the artificial intelligence tools and an analysis of previously stored information for the individual that enables an adaptation of the implantable intelligent data processing device.

22. The adaptive multi-level hierarchical control system of claim 1 wherein the at least one sensor detects physiological signals that indicate a state of brain activity in the individual.

* * * * *